(12) United States Patent
Malinge et al.

(10) Patent No.: US 9,701,956 B2
(45) Date of Patent: Jul. 11, 2017

(54) IN VITRO PRODUCTION OF DNA MINICIRCLES COMPRISING LESS THAN 250 BASE PAIRS

(71) Applicant: CENTRE NATIONAL DE LA RECHERCHE SCIENTIFIQUE, Paris (FR)

(72) Inventors: Jean-Marc Malinge, Olivet (FR); Patrick Midoux, Saint Denis de l'Hotel (FR); Thomas Thibault, Villedieu sur Indre (FR); Chantal Pichon, Saint Denis de l'Hotel (FR)

(73) Assignee: CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 0 days.

(21) Appl. No.: 14/647,044

(22) PCT Filed: Nov. 20, 2013

(86) PCT No.: PCT/EP2013/074316
§ 371 (c)(1),
(2) Date: May 22, 2015

(87) PCT Pub. No.: WO2014/079900
PCT Pub. Date: May 30, 2014

(65) Prior Publication Data
US 2015/0299692 A1    Oct. 22, 2015

(30) Foreign Application Priority Data
Nov. 22, 2012    (EP) .................................... 12306454

(51) Int. Cl.
*C12N 15/10* (2006.01)
*C12N 15/64* (2006.01)
*C12N 15/113* (2010.01)
*A61K 48/00* (2006.01)

(52) U.S. Cl.
CPC ............ *C12N 15/10* (2013.01); *C12N 15/113* (2013.01); *C12N 15/64* (2013.01); *A61K 48/00* (2013.01)

(58) Field of Classification Search
CPC .................................. C12N 15/10; C12N 15/64
See application file for complete search history.

(56) References Cited

U.S. PATENT DOCUMENTS

2007/0031378 A1    2/2007 Mayrhofer et al.

OTHER PUBLICATIONS

Pil et al. (PNAS 1993, vol. 90, pp. 9465-9469).*
Swinger et al. (J. Mol. Biol. 2007, vol. 365, pp. 1005-1016).*
Sugimura et al. (PNAS 2006 vol. 103, pp. 18510-18514).*
International Search Report, dated Feb. 20, 2014, in corresponding International Application No. PCT/EP2013/074316.
Markus Heine et al., "A new semi-synthetic method simplifying DNA Minicircle Production," Dec. 31, 2011, Retrieved from the Internet: URL: http://rentschler.de/fileadmin/Downloads/Poster/Rentschler-Poster-In-Vitro-2011_Handout.pdf.
Mark Kay et al., "A robust system for production of minicircle DNA vectors," Nature Biotechnology, vol. 28, No. 12, Dec. 2010, pp. 1287-1289+2.
Yongli Zhang et al. "High-throughput approach for detection of DNA bending and flexibility based on cyclization," Proceedings of the National Academy of Sciences of the United States of America, vol. 100, No. 6, Mar. 18, 2003, pp. 3161-3166.

* cited by examiner

*Primary Examiner* — Jon E Angell
(74) *Attorney, Agent, or Firm* — Young & Thompson

(57) ABSTRACT

A method for the in vitro production of DNA minicircles includes steps of: a) providing nicked double-stranded oligodeoxynucleotides bunt-ended substrates having at least one phosphorylated 5' end, b) performing a ligase-mediated circularization on a reaction mixture including the nicked double-stranded oligodeoxynucleotides substrates and a DNA bending protein, and c) obtaining DNA minicircles.

12 Claims, 6 Drawing Sheets

IN VITRO PRODUCTION OF DNA MINICIRCLES COMPRISING LESS THAN 250 BASE PAIRS

FIELD OF THE INVENTION

This invention relates to an improved method for the in vitro production of DNA minicircles, through a one-pot ligase-mediated circularization reaction of linear nicked double-stranded oligodeoxynucleotide in the presence of a DNA bending protein. The present invention also relates to supercoiled DNA minicircles having less than 250 base pairs and their use in gene therapy application.

BACKGROUND OF THE INVENTION

DNA minicircles are nano-objects of great interest both for basic research studies and for multiple applications in nanotechnology and nucleic acids medicine.

DNA minicircles, either double- or single-stranded, can be used as nanoscale building objects in structural DNA nanotechnology, a growing field of research. For example, DNA minicircles have been used as scaffold to assemble nanoarchitectures after the incorporation of G-quadruplexes, RNA hairpin or chemically functionalized oligonucleotide leading to the possibility to create molecular devices with a broad range of functions. The ability to create a controlled bend in a structural material is an important feature that has been exploited for nanomachine building. This biological application of DNA nanostructures represents a very young field of research that necessitates amounts of DNA minicircles building material.

DNA minicircles have also promising applications as new biologically active nucleic acid molecule in gene therapy approaches. In particular DNA minicircles can be used as inhibitors of specific gene expression, because they offer the exciting possibility to block the expression of critical genes through the inhibition of key players in transcription regulation (i.e. transcription factors) without any changes in functions of other genes. In particular, the delivery of circular nucleic acids in biological fluid is also known to present several advantages as compared to linear oilgonucleotides such as an increased stability thanks to resistance to exonucleases. It is also well recognized that reducing the size of DNA is beneficial in gene therapy approaches by improving cell DNA transfection and trafficking (Lukacs, G. L et al., 2000, J. Biol. Chem. 275, 1625-1629; Kreiss, P. et al., 1999 Nucleic Acids Res. 27, 3792-3798).

Furthermore, DNA supercoiling is a relevant structural characteristic in DNA-dependent cellular processes (Kanaar, R. and Cozzarelli, N. R., 1992 Curr. Opin. Struct. Biol. 2, 369-379; Baranello, L. et al., 2012, Biochim. Biophys. Acta 1819, 632-638). DNA minicircles present the advantage to mimics the DNA loops that are formed during essential DNA-dependent transactions, such as transcription, replication and recombination. Therefore the use of supercoiled minicircles may help investigate higher order DNA structure of biological relevance on the binding and activity of proteins implicated in the DNA metabolism (transcription factors and repair proteins for instance).

The use of plasmids designed for in vivo site specific recombination allows production of minicircle containing supercoiling (Fogg, J. M. et al., 2006, J. Phys. Condens. Matter 18, S145-S159) in milligram quantities for DNA, however, the direct production of chemically functionalized minicircles is impossible as a consequence to in cellulo minicircle production. Furthermore, the versatility of this approach for introducing customized DNA sequences is limited by the labor intensive method and the likelihood of sequence-dependent unpredictable negative effect on the recombination efficiency and the production of short DNA fragment smaller than 250 bp is inefficient. Heine et al. have described (in a poster retrievable from the internet: URL: http://rentschler.de/fileadmin/Downloads/Poster/Rentschler-Poster-In-Vitro-2011_Handout.pdf), a semi-synthetic method for the production of DNA minicircles, wherein linear substrates, obtained after plasmid digestion by restriction enzymes and a purification step, are circularized using a ligase enzyme to produce relaxed circular DNA. A DNA gyrase can be used after the circularization step for inducing DNA. However, this method does not describe the production of minicircles down to 250 base pairs.

Indeed, the construction of minicircles from short linear DNA fragments down to 250 base pairs (bp) and containing random sequences remains difficult because such DNA length is in the vicinity of the persistent length (about 150 bp/50 nm, the persistence length being a measure to characterize the stiffness regarding intrinsic DNA flexibility). As a consequence the yield of the monomolecular reaction, i.e. the circularization of DNA by closure of both DNA ends by enzymatic ligation, is weak as compared to that of the competitive bi- and multi-molecular reactions between DNA double helix even at low range of DNA concentration (less than 1 nM). Consequently, only a few in vitro methods have indeed been reported for ligase-mediated circularization of linear DNA fragments of less than 250 pb.

In the absence of bending proteins, a slight increase in the efficiency of the cyclization reaction has been achieved using specific sequences endowed with intrinsic bendability (so called adenine tracts) with the drawback to lose the possibility to incorporate freely DNA sequence of interest, such as consensus sequence for protein recognition (Zhang, Y. and Crothers, D. M., 2003, Proc. Nat. Acad. Sci. USA 100, 3161-3166). Another in vitro strategy has employed DNA substrates with very long cohesive ends allowing hybridization of their single-stranded region, to increase the overall yield of minicircle formation but a low DNA concentration used in the cyclization reaction and labor intensive preparation steps remain important drawbacks for minicircle quantitative production (Du, Q. et al., 2008, Nucleic Acids Res. 36, 1120-1128).

In the presence of a DNA bending protein, randomsequence DNA fragments have been used in DNA ligasedependent circularization reactions to determine the ability of various architectural proteins to induce DNA bending/flexibility. However, the nanomolar concentration range of linear DNA substrate is a limitation towards the possibility of minicircle production.

Lastly, to the applicant knowledge, none of the abovementioned cell-free methods showed the possibility to yield supercoiled small DNA minicircles.

Therefore there is still a need for a method allowing quantitative and efficient production of DNA minicircles, of length down to about 250 base pairs with controlled supercoiling and customized DNA sequences.

SUMMARY OF THE INVENTION

The applicants have now discovered that DNA substrate designed by introducing a DNA structure perturbation and used in a ligase-mediated circularization reaction in the presence of a bending protein, enables DNA circularization reaction at elevated DNA concentration to yield finally a minicircle devoid of the initial DNA structural perturbation.

This is an innovating and versatile method that allows one pot production of DNA minicircles with sequence of any base composition and position. The method also gives the opportunity to prepare DNA minicircles comprising less than 250 base pairs, relaxed or endowed with supercoiling and containing a variety of site-specifically placed chemical modifications, finally allowing direct functionalization of minicircles for biological and biochemical applications.

Therefore the present invention relates to a method for the in vitro production of DNA minicircles comprising steps of:
a) providing nicked double-stranded oligodeoxynucleotides blunt-ended substrates having at least one phosphorylated 5' end,
b) performing a ligase-mediated circularization on a reaction mixture comprising the said nicked double-stranded oligodeoxynucleotides blunt-ended substrates and a DNA bending protein.
c) obtaining DNA minicircles In a particular embodiment of the method according to the invention, the nicked double-stranded oligodeoxynucleotides blunt-ended substrates provided at step a) have two phosphorylated 5' ends, and the DNA minicircles obtained or recovered at step c) are double-stranded closed relaxed minicircles.

In another particular embodiment, the method of the invention, the nicked double-stranded oligodeoxynucleotides blunt-ended substrates provided at step a) have only one phosphorylated 5' end, and the DNA minicircles obtained or recovered at step c) are single-stranded DNA minicircles.

Still in another particular embodiment, the method of the invention comprises steps of:
a) providing nicked double-stranded oligodeoxynucleotides blunt-ended substrates having only one phosphorylated 5' end.
b) performing a ligase-mediated circularization on a reaction mixture comprising the said nicked double-stranded oligodeoxynucleotides substrates and a DNA bending protein
c) obtaining nicked double-stranded DNA minicircles,
d) adding a kinase to the nicked double-stranded DNA minicircles obtained at step c)
e) ligating the said nicked double-stranded DNA minicircles in the presence of a DNA intercalator
f) obtaining supercoiled DNA minicircles, According to the invention, the nicked double-stranded oligodeoxynucleotides blunt-ended substrates having at least one phosphorylated 5' end may comprise one or more protein putative binding sites and/or DNA binding sites and/or one or more chemical functionalities, and/or one or more DNA base mismatches.

Supercoiled DNA minicircles comprising less than 250 base pairs and possibly exhibiting one or more protein putative binding sites, and/or DNA binding sites, and/or one or more chemical functionalities and/or one or more DNA base mismatches are also an object of the invention.

Another object of the invention is a DNA minicircle according to the invention, for its use as a decoy agent in gene therapy application The invention also relates to a kit for the in vitro production of DNA minicircles comprising:
a) single-stranded complementary overlapping oligodeoxynucleotides for the production of nicked double-stranded oligodeoxynucleotides substrates
b) a DNA bending protein from the HMG box family, and
c) a ligase.

The invention also relates to a DNA minicircle according to the invention as decoy agent in gene therapy application.

Lastly, the invention relates to the use of a DNA minicircles according to the invention as substrate for DNA binding studies.

BRIEF DESCRIPTION OF THE FIGURES

FIG. 3: Linear nicked blunt-ended duplexes D9 to D13, formed as depicted in FIG. 1. The sugar-phosphate backbone of both strands is nicked at the location indicated by the black arrow. The presence of a transcription factor consensus sequence is indicated in bold (NF-κB: GGGACTTTCC; ETS1: GGAAGCACTTCC; STAT3: TTCCCGTAA) and the human telomeric sequence is underlined. The presence of G/T mismatch is shown by size increased of the characters.

FIG. 4: Linear nicked blunt-ended duplexes D14 to D21, formed as depicted in FIG. 1. The sugar-phosphate backbone of both strands is nicked at the location indicated by the black arrow. The presence of a chemical base modification within oligonucleotide is indicated as follows: biotin dT (▲); cyanine 3 dT (♣); carboxyfluorescein dT (■); 8-oxoguanine (x).

DETAILED DESCRIPTION OF THE INVENTION

Figure 1:
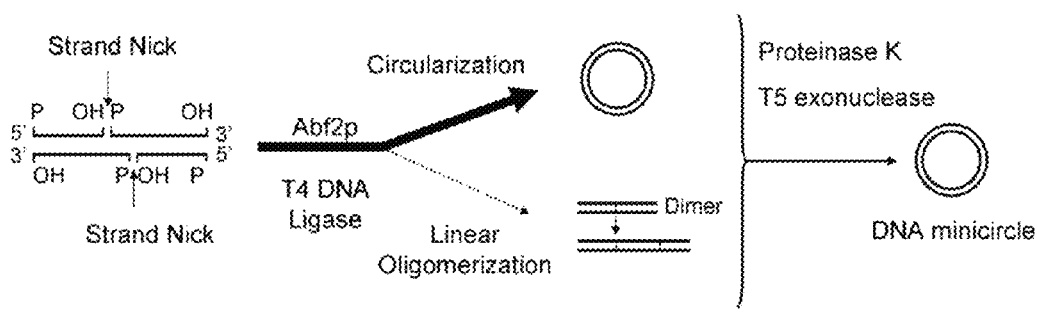
FIG. 1: (A) Scheme illustrating the method of DNA circularization with overlapping blunt-ended nicked DNA substrates for minicircle production. (B) Scheme showing the production of single nicked double-stranded DNA minicircle that can be used in turn for the production of either single-stranded minicircle (pathway 1) or relaxed or supercoiled double-stranded DNA minicircle (pathway 2).
Figure 1:
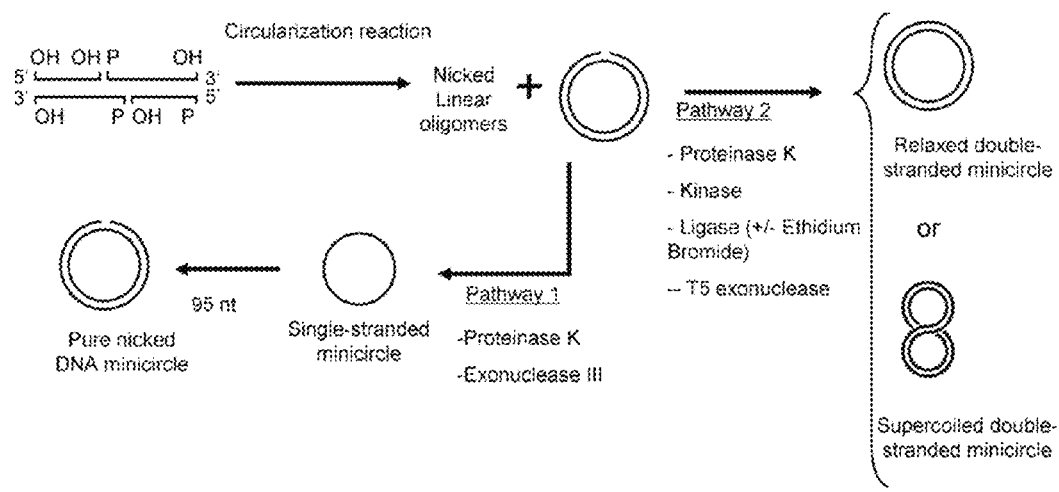

In the range of the DNA persistence length (less than 250, and in particular less than 150 bp), the intrinsic bendability of starting linear DNA is too weak for efficient circularization reaction by enzymatic ligation and the prevalence of the intermolecular reaction (DNA linear multimers formation) needs to perform reaction at very low DNA concentrations (in the nanomolar range) therefore limiting yields of production to nanogram quantities. The applicant has now designed a reaction allowing efficient circularization (e.g., with high yields) of DNA by enzymatic ligation at DNA concentrations at least two orders of magnitude greater than previously used. In the present invention, a DNA structure perturbation was introduced within the linear template DNA substrate to be circularized prior to the circularization reaction. Such structure potentiates the DNA binding activity of a DNA bending protein that in turn enables efficient ligase-mediated circularization reaction at elevated DNA concentration for production of DNA minicircle devoid of the initial DNA structure perturbation. This method therefore allows for the first time to produce efficiently DNA minicircles, relaxed or supercoiled, of less than 250 base pairs, with no sequence limitation.

1—Method According to the Invention

The present invention first relates to a method for the in vitro production of DNA minicircles comprising steps of:

a) providing nicked double-stranded oligodeoxynucleotides blunt-ended substrates having at least one phosphorylated 5' end, b) performing a ligase-mediated circularization on a reaction mixture comprising the said nicked double-stranded oligodeoxynucleotides substrates and a DNA bending protein.

c) obtaining DNA minicircles.

In other words, in step b), at least one ligase and at least one bending protein are added to the nicked double-stranded oligodeoxynucleotides substrates, allowing to obtain in one step, a DNA minicircle. Indeed, a ligase-mediated circularization according to the invention is an enzymatic ligation. According to the invention, a ligase is an enzyme that facilitates the joining of DNA strands together by catalyzing the formation of a phosphodiester bond between the 3' hydroxyl end of one strand and the 5' phosphate end of the other strand. DNA ligase activity has been extensively studied and was shown to be unaffected by histone proteins bound to nicked DNA substrate; this indicates that the bending protein should not compromise ligase activity with nicked DNA. DNA ligase enzymes that can ligate a DNA fragment having two blunt ends and overlapping region formed by overhanging complementary cohesive sequences are convenient to the invention. Typical ligases according to the invention are ATP-dependent ligases. In particular, a ligase according to the invention can be selected from the group consisting of T3 or T4 DNA ligase. For example, the T4 DNA ligase that is able to ligate cohesive or blunt ends and is commercially available and cheap is well suited according to the invention.

According to the invention, a DNA minicircle is a single- or a double-stranded circular DNA molecule of less than 1 kb in size. In particular, a DNA minicircle according to the invention comprises between 80 base pairs and less than 250 base pairs (bp). By less than 250 bp it is herein intended, less than 240, 230, 220, 210, 200, 190, 180, 170, 160, 150, 140, 130, 120, 110, 100, 90 bp. Typically, a DNA minicircle according to the invention contain between 80 and 200 bp, more particularly between 80 and 150 bp.

By DNA bending protein, it is intended herein a protein interacting with different conformational states of DNA and inducing DNA bends. A bending protein as used in the present invention binds DNA without substantial sequence specificity (nonspecific sequence binding) and without inducing cleavage of DNA chemical bonds (DNA backbone) or ligation of DNA strands; therefore bending proteins inducing cleavage of DNA strands for their functional activity are unsuitable for the present invention (gyrase, topoisomerase, recombinase, resolvase). Particularly well suited for the invention, are proteins which are easily and robustly produced and have ability to be active on DNA substrates containing different modifications including those induced by chemical groups as detailed further. Typically, a DNA bending protein, selected from the group comprising, or from the group consisting of: non-sequence specific proteins (NSS proteins) from the High Mobility Group (HMG) and the prokaryotic protein HU is suitable for the invention. This includes in particular proteins selected from the group comprising, or the group consisting of: HMGB1, NHP6A and the protein Abf2p, and more particularly the protein Abf2p.

Nicked double-stranded oligodeoxynucleotides substrates are double-stranded oligodeoxynucleotides having at least one internal nick per strand, such that they form an overlapping region. Such a nick according to the invention is notably illustrated on FIG. 1. It should be noted that the internal 5' ends formed by the internal nicks on each strand are also phosphorylated.

Nicked double-stranded oligodeoxynucleotides blunt-ended substrates are also named overlapping duplexes in the following of the application. The overlapping region between two nicks on each strand (overlapping inter-nick region) is typically between 10 and 20 bp, more particularly between 12 and 20 bp. Such an overlapping size allows obtaining a stable hybridization region. The presence of nicks in the DNA duplexes introduces DNA structure perturbation that help to induce some flexibility of the double helix (Furrer, P. et al., 1997, DNA J. Mol. Biol. 266, 711-721; Protozanova, E. et al., 2004, J. Mol. Biol. 342, 775-785), it is therefore a necessary condition according to the invention for efficient ligase-mediated DNA circularization in the presence of a DNA bending protein. By at least one internal nick, it is intended according to the invention that the overlapping duplexes may contain at least 1, 2 or 3 nicks per strand. Typically, overlapping duplexes according to the invention contain one nick per strand and per portion of 50-95 nucleotides. For example overlapping duplexes of less than 95 nucleotides can contain one nick per strand, overlapping duplexes having 95 to 180 nucleotides can contain one or two nicks per strand and overlapping duplexes having between 95 to 180 nucleotides can contain two or three nicks per strand.

In a particular embodiment of the invention, overlapping duplexes contain more than 80 bp and less than 250 bp. By less than 250 bp, it is herein intended, less than 240, 230, 220, 210, 200, 190, 180, 170, 160, 150, 140, 130, 120, 110, 100, 90 bp. Typically overlapping substrates according to the invention contain between 80 and 250 bp and more precisely between 80 and 200 bp. In some instances, overlapping substrates according to the invention contain between 84 and 200 bp.

The nicked double-stranded oligodeoxynucleotides substrates according to the invention have blunt ends. The nicked double-stranded oligodeoxynucleotides substrates according to the invention can be achieved with commercially available oligonucleotides, by assembling appropriate overlapping single-stranded oligonucleotides in order to form, for example, a starting blunt-ended DNA substrate of interest containing internal nicks as described above. In this context, commercial single-stranded oligonucleotides comprising between 40 and 60 nucleotides in length, as obtained for example by classical chemical approach of oligonucleotide synthesis such as the solid-phase phosphoramidite method are well suited for the invention. Indeed, the possibility of using synthetic oligonucleotides in the present method has several advantages: they are easily manufactured with large scale and low cost and they show the ability to carry an unlimited combination of sequence information with or without chemical modifications.

Step c) of the method according to the invention consists in obtaining (or recovering) the DNA minicircle.

In some instances, the DNA minicircle to be obtained, forms part of a composition. Typically, the said composition comprises the reaction mixture that contains the DNA minicircle. In particular embodiments of the method, the said composition consists in the reaction mixture that contains the DNA minicircle to be obtained.

In other instances, an isolated DNA minicircle of the invention can also be recovered with respect to the complex reaction mixture from which it occurs. An "isolated" nucleic acid molecule, e.g., an isolated DNA minicircle according to the invention, as used herein, is one that is separated from other nucleic acids comprising different topologies (such as linear oligomers), sizes and/or sequences and/or proteins that are present in the one-pot reaction mixture. Such isolated molecules have been completely or partially purified from these other nucleic acids and proteins. An isolated nucleic acid molecule of the invention can comprise at least about 50, 80 or 90% (on a molar basis) of all macromolecular species and proteins present.

Recovery of isolated DNA minicircles can be achieved according to classical techniques of the art. For example, recovery can be made by ethanol precipitation or using silica bead for DNA purification.

In certain embodiments of the method, the step c) of obtaining DNA minicircle can comprise the addition of at least an enzyme selected from the group consisting of the proteases and the nucleases, and more particularly the group consisting of the protease and the exonucleases. Typically addition of an exonuclease allows the elimination of the nicked strand of nicked double-stranded DNA minicircles, in order to obtain single-stranded DNA minicircles.

When an isolated DNA minicircle is recovered at step c), said step c) can also comprises a supplementary sub-step of eliminating reaction contaminants, which are typically nucleic acids and proteins from the reaction. DNA contaminants are typically nucleic acids comprising different topologies, such as unproductive linear DNA, linear oligomers and in some instances, the nicked strand of circular DNA minicircles. Protein contaminants are notably the bending protein as well as the various enzymes that are used during the one pot reaction, such as ligases, digestion enzymes and kinases. Therefore, elimination of reaction contaminants preferentially comprises the addition of at least an enzyme selected from the group consisting of proteases and nucleases.

In some instances, elimination of reaction contaminants can comprise the addition of at least one protease and at least one nuclease. Said at least one protease and at least one nuclease can be added simultaneously or sequentially. Typically, nucleases are exonucleases. In other instance, elimination of reaction contaminants comprises the addition of a protease and in more particular cases the elimination of reaction contaminants consists in the addition of a protease.

According to the invention, DNA contaminants can be removed by nuclease enzymes, which are capable of cleaving the phosphodiester bonds between the nucleotide subunits of nucleic acids. Well-suited nucleases according to the invention are nucleases that are able to initiate nucleotide removal from the 5' or the 3' termini or at gaps and nicks of linear or circular double-stranded DNA. Depending on the embodiment of the invention nucleases having only exonucleasic activity (i.e.: that work by cleaving nucleotides one at a time from the end (exo) of a polynucleotide chain) such as: exonuclease III, exonuclease I, or nucleases having exonucleasic activity and only a weak single-stranded endonucleasic activity (i.e.: that cleave the phosphodiester bond within a polynucleotide chain), such as T5 exonuclease, can be used. In a particular embodiment of the invention, exonucleases that do not degrade supercoiled double-stranded DNA, such as T5 exonuclease, are preferred.

According to the invention, protein contaminants can be removed by enzymes from the group of proteases that conducts proteolysis, (i.e.: begins protein catabolism by hydrolysis of the peptide bonds that link amino acids together in the polypeptide chain forming the protein), such as serine proteases, threonine proteases, cysteine proteases, aspartate proteases, metalloproteases, glutamic acid proteases. Proteases, such as broad-spectrum serine proteases, that are commonly used in molecular biology to digest protein and remove contamination from preparations of nucleic acid are particularly well suited for the invention. Broad-spectrum serine proteases having autolytic activity, such as (but not limited to) proteinase K, are convenient for the invention. For example, Pronase® that is a commercially available mixture of proteinases isolated from the extracellular fluid of *Streptomyces griseus* is also well convenient to the invention. At least 10 proteases are in the pronase mixture, five serine-type proteases, two zinc endopeptidases, two zinc leucine aminopeptidases and one zinc carboxypeptidase. Digestion with pronase is known to be useful when extensive or complete degradation of protein is required.

Preferentially, removal of proteins and DNA contaminants is made by sequential addition of at least a protease and at least an exonuclease.

The method according to the invention involves enzymatic reactions that are well known in classical techniques of molecular biology, such that determination of the specific characteristics regarding reagent concentrations, incubation times and temperature is well within the skill of the man of the art. In particular, the amount of the various components used for the different steps of the method will be adapted by the man skilled in the art. Typically, DNA vs. bending protein ratio is from 0.5 to 2, and the DNA vs. ligase ratio is from 2 to 8. More particularly, the DNA/Abf2p ratio ranges from 0.5 to 2 and the DNA/T4 ligase ratio ranges from 2 to 8.

In a particular embodiment of the method according to the invention, the nicked double-stranded oligodeoxynucleotides substrates provided at step a) of the method have two phosphorylated 5' ends and the DNA minicircles that are obtained at step c) are double-stranded closed DNA minicircles.

One strategy for such minicircle production is notably outlined in FIG. 1A. In this strategy, step c) comprises elimination of reaction contaminants for recovery of isolated DNA minicircles. Preferentially, elimination of reaction contaminants can be obtained by sequential addition of at least a protease followed by addition of at least an enzyme having exonucleasic activity. A final addition of protease may be also required for elimination of the exonuclease.

In another particular embodiment of the method of the invention, the nicked double-stranded oligodeoxynucleotides substrates provided at step a) of the method have only one phosphorylated 5' end and the DNA minicircles that are obtained at step c) are single-stranded DNA minicircles.

In such a case, the circularization reaction occurs by sealing DNA ends of one strand to form a double-stranded DNA minicircle containing a single nick in the other.

In such embodiment, step c) comprises elimination of reaction contaminants. Indeed, addition of a nuclease having exonucleasic activity is required for eliminating the nicked-strand of the DNA minicircle and recovering a single-strand DNA minicircle. Addition of a protease can further be used for digestion of protein contaminants.

For example, elimination of reaction contaminants can be performed by sequential addition of at least a protease, such as proteinase K, followed by addition of at least an exonuclease, such as exonuclease III. A final addition of protease may be also required for elimination of the exonuclease. This embodiment of the invention allows obtaining pure single-stranded DNA minicircles that can be used for further DNA molecules assemblages.

In some instances, this embodiment of the method comprises a step d) consisting of adding a linear oligonucleotide complementary to the strand having an unphosphorylated 5' end of the nicked double-stranded oligodeoxynucleotides substrates strands of step a) and a step e) consisting in obtaining (or recovering) nicked double-stranded DNA minicircles.

This embodiment of the method according to the invention allows obtaining pure nicked double-stranded DNA minicircles.

According to the invention hybridization of the single-stranded DNA minicircle can be performed with a complementary linear oligonucleotide in order to obtain a double-stranded DNA with one nick or with n complementary oligonucleotides in order to obtain a double-stranded DNA minicircle with (n−1) nicks.

One strategy for obtaining single-stranded minicircles as well as pure nicked double-stranded DNA minicircles is outlined in FIG. 1B, pathway 1.

In a last embodiment of the method for obtaining DNA minicircles according to the invention comprises the following steps:
a) providing nicked double-stranded oligodeoxynucleotides substrates having only one phosphorylated 5' end.
b) performing a ligase-mediated circularization on a reaction mixture comprising the said nicked double-stranded oligodeoxynucleotides substrates and a DNA bending protein
c) obtaining nicked double-stranded DNA minicircles,
d) adding a kinase to the nicked double-stranded DNA minicircles obtained at step c).
e) ligating the said nicked double-stranded DNA minicircles in the presence of a DNA intercalator
f) obtaining double-stranded supercoiled DNA minicircles.

In such embodiment, step c) comprises the addition of at least a protease, for eliminating reaction contaminants and in particular the DNA bending protein. Preferentially, step c) comprises the addition of a protease for eliminating protein contaminants from the reaction mixture. In some instances, the protease of step c) can be added in such amount quantity that both the bending protein and ligase protein are digested in addition to the protease thanks to its self-digestion activity. In such case, no exonuclease is added in order to avoid digestion of the nicked strand of double-stranded DNA minicircles.

Religation of nicked circular DNA plasmid in the presence of an intercalating drug, such as Ethidium Bromide (EtBr), is known to introduce unwinding by decreasing the twist (Tw) value of dinucleotide steps from 34° to 26° (Bates, A D and Maxwell, A, 2005, Oxford Univ. Press $2^{nd}$ ed., 25-81)). Sealing of the nick by enzymatic ligation will fix the unwinding and removal of the intercalating drug will induce an increase in the twist value and therefore in the number of base pairs per helix turns. As a consequence the double-stranded DNA minicircle is underwound with torsional stress and the linking number Lk of the minicircle decreases (Lk being the number of times that each DNA strand winds around the other in circular DNA). Changes in the linking number ($\Delta Lk$) is the difference between Lk and $Lk_0$ (the number of double helical turns in the original linear molecule is equal to N/h with N being the DNA length in base pairs and h the helical repeat with a value of 10.54 bp/turn); variation in linking number generally induces apparition of supercoiling or writhe (Wr), e.g., an helix coiling upon itself, allowing formation of usually one lowest energically shape of circle called a topoisomer, each topoisomer of the same molecule migrating separately on gel electrophoresis. Such geometric variations of circular DNA are summarized by the following equation: $\Delta Lk = \Delta Tw + \Delta Wr$ where any change in linking number relates to a change in the writhe and/or the twist and vice versa. In the present situation, the decrease in Lk yields a negative value for $\Delta Lk$ corresponding to a situation where the molecule is underwound with the possibility of negative supercoiling formation. For instance if the linking number is decreased by one within minicircle after ligation and removal of EtBr, then $\Delta Lk = -1$; $\Delta Tw$ is equal to zero because the unwinding value Tw is the same as within normal DNA in the absence of EtBr then we can deduce that $\Delta Wr$ is equal to −1 (minicircle topoisomer with one superhelical turn). This is exemplified with minicircle of 95 bp where values of $\Delta Lk$ are indicated.

Suitable DNA intercalators according to the invention include, but are not limited to, ethidium bromide (EtBr) and chloroquine. The list of potential intercalators known in the art is extensive, as many drugs have been developed that act through intercalation such as, for example, m-AMSA, daunorubicin and doxorubicin. In addition, there are a number of fluorescent DNA stains that bind through intercalation. These include, for example, EtBr, acridine orange and propidium iodine.

Preferentially step e) of re-ligation of the nicked DNA minicircle in the presence of a DNA intercalator is preceded by a d) step consisting of adding a kinase to the reaction mixture comprising the nicked double-stranded DNA minicircles obtained at step c). Addition of a kinase allows the transfer of a phosphate from ATP to the 5"-terminus of the nicked strand. Suitable kinases according to this embodiment include, but are not limited to, polynucleotide 5'-hydroxyl-kinases and typically the T4 polynucleotide kinase. Removal of the DNA intercalator can be achieved typically by butanol extraction.

In step f), supercoiled DNA minicircles can be recovered as a part of a composition comprising the reaction mixture or isolated according to well-known methods of the art, such as described above, and for example by ethanol precipitation or using silica beads DNA extraction. In some instances, step f) comprises addition of at least an enzyme selected from the group consisting in the protease and the exonucleases. Advantageously, step e) comprises the addition of at least an exonuclease in order to eliminate nucleic acid contaminants such as linear oligomers. More particularly, step f) consists in adding at least an exonuclease.

A strategy for obtaining supercoiled DNA minicircles according to the invention is notably outlined in FIG. 1B, pathway 2.

To the applicant's knowledge, it is the first time that supercoiling is observed in a small minicircle of 95 bp. Further the method of the invention allows production of supercoiled DNA minicircles in one pot; the first topoisomer ($\Delta Lk=-1$) has a negative superhelical density of 0.1 which is slightly more elevated than that expected in physiological conditions (about 0.08) (Zechiedrich, E. L. et al., 2000, J. Biol. Chem. 275, 8103-8113) and thus can be used to study the effect of supercoiling in bent DNA molecule on DNA binding activity of proteins.

The present invention further allows choosing the nature and position of DNA sequences of the DNA minicircles. Indeed it has been demonstrated by the applicant that the ligase-mediated circularization of the invention can be obtained with overlapping duplexes of any sequence. As mentioned above, the use of synthetic oligonucleotides in the present method has several advantages: they are easily manufactured with large scale and low cost and they show the ability to carry unlimited sequence functionalizations (or modifications) including, but not limited to, specific binding sites, DNA base mismatches or chemical functionalities.

Therefore in the method of the invention, nicked double-stranded oligodeoxynucleotides substrates having at least one phosphorylated 5' end comprise at least one sequence functionalization selected from the group consisting of: protein putative binding sites, DNA binding sites, chemical functionalities, DNA base mismatches. According to the invention, typical protein putative binding sites are binding sites for DNA binding proteins.

DNA binding proteins of interest include, but are not limited to topoisomeases, restriction endonucleases, transcription factors, remodeling factors, helicases, polymerases, telomeric protein, DNA repair proteins, DNA methylases, and architectural proteins. Typically, transcription factors include, but are not limited to, E2F, NF-kB, STAT 3, TAR, ETS1, ATF4, AP1, TWIST, SNAIL, NRF2, HIF and OCT4.

For example, an overlapping duplex according to the invention can contain at least one, typically 1 to 10, and more particularly 1 to 6 protein putative binding sites.

Said overlapping duplex can also contain at least one and preferentially several (1, 2, 3, 4, 5, 6, 7, 8, 9, 10, and more) chemical functionalities that can be the same or different.

Typical chemical functionalities include, but are not limited to, site-specifically placed base modifications and site-specifically placed linkers or site-specifically placed labels. Indeed, overlapping duplexes according to the invention, functionalized with various base analogs and modifications, can be easily obtained for example from commercially available synthetic DNA oligonucleotides in the course of solid support synthesis, and the applicant has demonstrated that the circularization reaction according to the invention is permissive for chemically modified oligonucleotides.

Typical base modifications according to the invention are for example the one that are the substrates of protein selected from the group comprising DNA repair proteins, and DNA alkyltransferases (or DNA methyltransferases). DNA repair proteins include but are not limited to proteins involved in base excision repair (such as, but not limited to, DNA glycosylases, AP endonucleases, end processing enzymes and DNA ligases), proteins involved in nucleotide excision repair (such as, but not limited to, XPA, XPB, XPC, XPD, XPE, XPF, and XPG that derive from Xeroderma pigmentosum, or CSA and CSB that represent proteins linked to Cockayne syndrome, or the proteins ERCC1, RAD23A, RAD23B), and proteins involved in the mismatch repair system.

Bases modifications, according to the invention, are also the one that can be naturally formed when DNA is subjected to oxidative conditions, ionizing radiations or sunlight.

Example of base modifications according to the invention are oxidized bases (such as, but not limited to, 8-oxoguanine, 2,6-diamino-4-hydroxy-5-formamidopyrimidine (FapyG), 4,6-diamino-5-formamidopyrimidine (FapyA), thymine glycol, thymidine glycol, cyclo-dA and cyclo-dG as well as pyrimidine dimers), alkylated bases (such as, but not limited to, O$^6$MethylGuanine), deaminated bases (such, but not limited to, as hypoxanthine formed from deamination of adenine, xanthine formed from deamination of guanine) and other hydrolyzed bases such as depurination and depyrimidination, and uracil inappropriately incorporated in DNA, or formed by deamination of cytosine.

Typical base modifications according to the invention are the 8-oxoguanine, thymine glycol base modifications, which are substrates for base excision repair, the thymine dimer, and base cyclo-dA which are substrates for nucleotide excision repair.

Base modifications also include various sequences such as at least one, and preferentially 1 to 10, purine- or pyrimidine-rich sequences that are typically used for Hoogsteen base pairing of a third strand, guanine rich sequences that allow quadruplex formation, or the human telomeric sequence.

Typical site-specifically placed linkers include but are not limited to: Acrydite™, Adenylation, IDT's Azide modification, Digoxigenin modification, Cholesteryl-TEG, Amino-Modifiers, fluorescent dyes, Alkynes, Biotinylation, Thiol Modifications.

Said linkers and typically amino-modifiers such as amino-modifier dT, enable further site-specific functionalization by various chemical entities including but not limited to: molecular labeling, peptide polymers, for example through the well-known N-hydrosuccinimide coupling reaction.

Typical site-specifically placed labels according to the invention include, but are not limited to haptens, such as biotin or digoxigenin, radioactive isotopes, such as $^3$H or $^{32}$P, fluorescent dyes such as Cyanin 3 or carboxyfluorescein.

Another object of the invention relates to a method for identifying DNA binding protein, comprising steps of:
   isolating a supercoiled DNA minicircle of less than 250 bp and comprising at least one putative protein binding site according to the invention;
   contacting the said DNA minicircle with a protein of interest under conditions suitable for DNA binding; and
   assaying for DNA binding,
wherein DNA binding is indicative of a DNA binding protein.

Further another embodiment of the invention relates to: a method for screening for modulators of DNA binding proteins, comprising:
   contacting a DNA binding protein of interest with a DNA minicircle according to the invention under conditions suitable for DNA binding in the presence and absence of a test agent; and
   quantifying the amount of DNA binding in the presence and absence of the test agent,
wherein altered DNA binding is indicative of the test agent's being a modulator of DNA binding.

According to the invention, DNA minicircles can be attached to, for example, a solid support (column chromatography matrix, wall of a plate, microtiter wells, column pore glass, pins to be submerged in a solution, beads, etc.). Accordingly, DNA minicircles can be fixed to a solid phase directly or indirectly, e.g., by a linker or other molecules. Examples of such solid supports include, but are not limited to, plastics such as polycarbonate, complex carbohydrates such as agarose and sepharose, and acrylic resins such as polyacrylamide and latex beads. Techniques for coupling nucleic acid probes to such solid supports are well known in the art.

Typically, DNA minicircles of the invention can be linked to various materials such as i) agarose beads for the search of protein binding within cell-free extract ii) microplate or sensor chip iii) quantum dots or antibodies iiii) magnetic particles, for molecular biology and gene therapy applications.

For example, biotinylated minicircles can be linked to various streptavidin coated materials such as i) streptavidin agarose beads ii) streptavidin coated surface such as microplate or sensor chip iii) quantum dots or antibodies through streptavidin interaction iiii) streptavidin-coated magnetic particles.

2—DNA Minicircles and Kits According to the Invention

Another object of the invention related to DNA minicircles obtainable by the method of the invention.

The following embodiments of minicircles according to the invention can be taken both individually and in combination.

In one embodiments DNA minicircles comprises more than 70 bp and less than 250 bp as mentioned above in the method of the invention. Typically, a minicircle according to the invention comprises between 80 and 200 bp, more particularly between 84 and 200 bp.

In another embodiment of the invention, the minicircles of the invention are endowed with supercoiling forming several topoisomers depending on the length of DNA minicircle (three topoisomers with 95 bp minicircles as exemplified).

In a further embodiment of the invention, DNA minicircles of the invention can also comprise various sequence functionalizations (or modifications), such as protein putative binding sites, DNA binding sites, chemical functionalities and DNA base mismatches as described above. Typical chemical functionalities include, but are not limited to, site-specifically placed base modifications and site-specifically placed linkers or site-specifically placed labels as described above.

According to the invention DNA minicircles comprise at least one sequence modification selected from the group consisting of: protein putative binding sites, DNA binding sites, chemical functionalities (or modification), and DNA base mismatches.

Typically, a DNA minicircle according to the invention contains 1 to 10 putative protein binding sites and can further contain at least one and more preferentially several chemical modifications and or DNA base mismatches; the chemical modifications being the same or different.

In some embodiments of the invention, DNA minicircles are therefore substrates for various DNA binding proteins such as DNA repair protein, topoisomeases, restriction endonucleases, transcription factors, remodelling factors, helicases, polymerases, telomeric protein, DNA methylases, and architectural proteins.

In one embodiment of the invention a DNA minicircle according to the invention contain at least 1 to 6 κB binding sites. In a more particular embodiment of the invention said minicircle can comprise at least one further protein putative binding sites for at least one further protein of interest. Said protein of interest can be DNA repair proteins or transcription factors such as E2F, NF-kB, STAT 3, TAR, ETS1, ATF4, AP1, TWIST, SNAIL, NRF2, HIF, Oct4, and in particular, ETS1 and/or STAT3.

The presence of several protein binding sites allows the building of nucleic acid platforms with multiple protein interactions.

In some instance, said DNA minicircle can further comprise at least one chemical modification.

Chemical functionalities comprise site-specifically placed base modifications and site-specifically placed linkers or site-specifically placed labels.

DNA minicircle containing amino-modifier, such as for example amino-modifier dT could further enable site specifically functionalization (or modification) of the minicircle by various chemical entities (molecular labeling, peptides, polymers) thanks to the well-known N-hydroxysuccinimide coupling reaction. Such functionalization could endow minicircles with new important properties for biological applications such as cell targeting, cell delivery and cell trafficking.

Minicircles with fluorescent labeling can be used in various studies such as i) structural investigation of minicircle in the presence or absence of proteins through Förster resonance energy transfer (FRET) thanks to appropriately placed chromophores ii) cell uptake and trafficking of minicircles for biological applications.

Another object of the invention relates to a DNA minicircle according to the invention, for its use as a decoy agent in gene therapy application.

According to the invention a decoy agent is a DNA minicircle comprising at least one putative binding site for a DNA binding protein, preferentially a transcription factor, and that is therefore able to compete for binding of the said DNA binding protein with consensus sequences in target genes. Transcription factors bind specific sequences found in the promoter regions of genes (target genes) whose expression they then regulate (switch on or off). These binding sequences are generally 6-10 base pairs in length and are occasionally found in multiple copies within the promoter regions of target genes. Therefore if delivered into the cell in sufficient concentrations, the decoy agent has the potential to attenuate the binding of the protein, typically a transcription factor to promoter regions of target genes and thus attenuate the function of the transcription factor to regulate the expression of its target gene(s).

NF-κB is a transcription factor that plays a pivotal role in the coordinated transactivation of cytokine and adhesion molecule genes whose activation is involved in the pathogenesis of numerous diseases, e.g. cancer and arthritis. Indeed, target genes of NF-κB are inflammatory and immuno-regulator genes as well as antiapoptotic genes and genes regulating the cell growth.

Another attractive transcription factor as therapeutic target is Stat3, which is activated in several human cancers and participate in cancer cell proliferation.

Still another transcription factor of particular interest according to the invention is the transcription factor ETS1 whose expression is increased in several solid tumors and participates in angiogenesis and metastasis invasion.

Therefore a particular objet of the invention relates to DNA minicircles containing one or more binding site for NF-κB and/or STAT3 and/or ETS1, more particularly 1 to 10 NF-κB binding sites, and/or 1 to 10 STAT3 binding sites and/or 1 to 10 binding sites for ETS1, and even more particularly 1 to 6 NF-κB binding sites and/or 1 to 6 STAT3 binding sites and/or 1 to 6 ETS1 binding sites, for its use for regulating or attenuating the expression of target genes in gene therapy of inflammatory diseases such as cancer or cardiovascular diseases. Indeed, a multitargeting minicircle as illustrated for duplex D11 which directed towards these three transcription factors could be used in a multitargeting decoy strategy.

Minicircle containing appropriate DNA sequences could also be modified by an alkylating agent, such as metal based drug (for example but not limited to cisplatin), to form DNA lesions that can in turn attract target proteins and in particular DNA repair proteins such as nucleotide excision repair proteins (for example ERCC1-XPF). Using the platinated DNA minicircle in decoy strategy could increase chemotherapy efficacy of DNA alkylating drugs by inhibiting DNA repair proteins in resistant cancer cells that are known to repair actively drug DNA lesions.

Still another object of the invention is a kit for the in vitro production of DNA minicircles comprising:
 a) single-stranded complementary overlapping oligodeoxynucleotides for the production of nicked double-stranded oligodeoxynucleotides substrates
 b) at least one DNA bending protein, and
 c) at least one ligase.

In some instance, the said kit comprises:
 a) single-stranded complementary overlapping oligodeoxynucleotides for the production of nicked double-stranded oligodeoxynucleotides substrates
 b) a DNA bending protein, and
 c) a ligase.

In another embodiment the kit according to the invention comprises:
 a) nicked double-stranded oligodeoxynucleotides substrates according to the invention.
 b) at least one DNA bending protein, and
 c) at least one ligase.

In some instance, the said kit comprises:
 a) nicked double-stranded oligodeoxynucleotides substrates according to the invention.
 b) a DNA bending protein, and
 c) a ligase.

3—Uses According to the Invention

Another object of the invention relates to the use of a DNA minicircle according to the invention as a substrate for DNA binding studies. Indeed in an embodiment of the invention, the DNA minicircles according to the invention can be used to screen for agent that bind to DNA. Typically, such minicircles are engineered to contain at least one putative binding site for at least one DNA-binding protein of interest.

Protein of interest according to the invention can be selected from the group comprising: topoisomerases, restriction endonucleases, transcription factors, remodelling factors, helicases, polymerases, telomeric protein, DNA repair proteins, DNA methylases, and architectural proteins. Preferentially, proteins of interest are DNA repair proteins and transcription factors. Typically, transcription factors include, but are not limited to, E2F, NF-kB, STAT 3, TAR, ETS1, ATF4, AP1, TWIST, SNAIL, NRF2, HIF and Oct4.

More particularly, DNA minicircle according to the invention and carrying at least one sequence functionalization (or modification) as described above (typically at least one putative binding site for at least one DNA-binding protein) can be used to target and possibly titrate said proteins in cell.

As described above sequence functionalizations (or modifications) according to the invention include, but are not limited to, specific binding sites, DNA base mismatches or chemical functionalities. Chemical functionalities comprise site-specifically placed base modifications and site-specifically placed linkers or site-specifically placed labels.

Several proteins from base and nucleotide excision repair systems are overexpressed in cancer cells and contribute to poor response to chemotherapy and/or radiotherapy. Therefore DNA minicircles chemically modified with at least one trapping lesion of interest could be used to titrate target proteins from the above mentioned repair system in decoy strategy approaches.

Further, a variety of modified bases, such as $O^6$MethylGuanine or methylated cytosine, can also be incorporated within DNA minicircles with the purpose to trap several target proteins implicated in cancer. Such proteins are typically repair proteins (such as, but not limited to, $O^6$alkylguanine-DNA alkyltransferase, or $O^6$MethylGuanine-DNA methyltransferases), and DNA methyltransferases (such as, but not limited to, cytosine-5 methyltransferase).

Another particular embodiment of the invention relates to the use of a DNA minicircle, relaxed or endowed with supercoiling, and comprising at least one putative binding site for at least one DNA-binding protein, as a decoy nucleic acid for the study of endogenous gene regulation in vivo as well as in vitro.

Because DNA minicircles cannot be replicated in cells, the inhibition of a target protein (decoy effect) is transient which may be advantageous in some applications where a drug like approach to gene inhibition is useful but a drawback when permanent transformations is desired. In such a case, irreversible trapping of a target protein should be an advantage to postpone the negative effect of the minicircle by including chemical functionalities allowing DNA-protein covalent linkage.

The delivery of circular nucleic acids in biological fluid is also known to present several advantages as an increased stability thanks to resistance to exonucleases. The size of the minicircles also authorizes the presence of several protein binding sites opening the way to the building of nucleic acids platforms with multiple proteins interactions.

In non-viral gene therapy, DNA diffusion in the cytoplasm and nuclear import are believed to be rate-limiting determinants for transgene delivery, which is performed with the use of circular supercoiled plasmid DNA. Studies of DNA mobility in cells have been carried out as a function of the DNA size using linear DNA, which does not mimic circular DNA as a consequence to DNA ends effects.

Therefore, a particular embodiment of the invention is the use of DNA minicircles according to the invention for the study of therapeutic nucleic acids trafficking in cells, such as plasmid used in gene therapy as a function of several DNA parameters (sequence, topology).

DNA minicircles according to the invention, single- or double-stranded, relaxed or endowed with supercoiling and/or containing at least one sequence functionalization as described above can be used in various applications.

For example, DNA minicircles can be used for further DNA assemblages as well as in various biological applications involving cell targeting delivery and trafficking.

Another example relates to the use of relaxed or supercoiled DNA minicircles according to the invention to study the mutual influence of DNA topology and bending.

DNA minicircle according to the invention, relaxed or endowed with supercoiling and with customized sequences (e.g., having at least one chemical functionalities including site-specifically placed base modifications and site-specifically placed linkers or site-specifically placed labels) can be used for the design of nano-scaled objects in structural DNA nanotechnology.

Lastly, DNA minicircle according to the invention can support Phi 29 DNA polymerase amplification for overproduction of linear single-stranded or double-stranded DNA of same sequence and length as the starting DNA minicircle, and for DNA sequencing.

EXAMPLES

1—Material and Methods

Oligodeoxynucleotides used here were synthesized by phosphoramidite method with or without modifications as indicated in the text and were purchased from Eurogentec (Seraing, Belgium). Proteinase K, T4 DNA ligase, T4 polynucleotide kinase and Exonuclease III were purchased from Fermentas and T5 exonuclease was from New England Biolabs. Full length NF-κB p50 and Fpg were bought from Promega and New England Biolabs, respectively. BaI31 nuclease and streptavidin were respectively from New England Biolabs and Sigma-Aldrich and 700 bp ladder DNA molecular weight marker was from Fermentas.

p-ET15 b derived vector containing Abf2p gene was kindly provided by F. Culard (Centre de biophysique moléculaire, CNRS, Orleans, France); the plasmid was used for transformation of BL21 (DE3) pLysS (Novagen) with 34 μg/ml of chloramphenicol and 30 μg/ml of kanamycin. The strain transformed was grown at 37° C. with shaking to an A600 of 0.5. The culture was induced with isopropyl-1-thio-β-D-galactopyranoside (Calbiochem) at a final concentration of 100 μM for 6 h. After centrifugation, the cells were resuspended in a sonication buffer (50 mM Tris-HCl pH 8.0, 500 mM NaCl, 20 mM imidazole, 5 mM β-mercaptoethanol) supplemented with protease inhibitor mixture (Sigma-Aldrich) and 100 mM phenylmethylsulfonylfluoride (Pierce) and then sonicated. All purification steps were performed at 4° C. The lysate obtained after centrifugation of the extract was applied to a nickel agarose column (Qiagen) and histidine-tagged Abf2p was eluted with buffer containing 100 mM imidazole at a flow rate of 1 ml/min. Abf2p was concentrated on an Amicon Ultra-4 10K (Millipore) and was stored at −70° C. in a buffer containing 25 mM Tris-HCl pH 8.0, 100 mM NaCl, 1 mM dithiothreitol (DTT) and 5% glycerol. Protein concentration was determined by using the Bradford reagent (Bio-Rad) using BSA as a standard. The final concentration of the protein was 3 mg/ml. The purity was estimated as >95% on sodium dodecyl sulfate-acrylamide gel using EZBlue gel staining reagent (Sigma).

Circularization Reaction

Method of Production of Double-Stranded Closed Relaxed Minicircle:

Preparation of each overlapping DNA templates were performed by mixing equimolar quantities of complementary single-stranded oligonucleotides in buffer containing 10 mM Tris-HCl and 25 mM NaCl, pH 7.5 at a concentration of 40 μM (expressed in mole of overlapping duplex); hybridization was carried out by heating the oligonucleotide mixture at 80° C. followed by slow cooling at a temperature of 15° C. in a water bath.

A standard reaction of circularization was carried out by adding the overlapping nicked duplex at a final concentration of 2 μM in a buffer containing 40 mM Tris-HCl, 10 mM MgCl$_2$, 10 mM DTT, 0.5 mM ATP and 5% glycerol, pH 7.8. Abf2p was next added to a final concentration of 2 μM followed by T4 DNA ligase (20 units); the reaction mixture was then incubated at 20° C. for 1 h followed by the addition of proteinase K (0.3 units); after an incubation time of 30 min at 55° C., exonuclease T5 was added (200 units) and incubation lasted for 30 min at 37° C.; finally a second digestion step by proteinase K was carried out. The minicircle was then precipitated by addition of AcONH$_4$ to a final concentration of 2.5 M and addition of 2 volumes of cold ethanol. After centrifugation at 14000 rpm for 15 min, the supernatant was discarded and the pellet washed by addition of 70% ethanol followed by centrifugation. The pellet was then resuspended in buffer containing 10 mM Tris-HCl, 1 mM EDTA pH 7.5 at a concentration of about 200 μg/ml in DNA minicircle; the optical density of DNA minicircle sample was measured for concentration determination and to control that the A260/A280 ratio was larger than 1.8 corresponding to high quality DNA. The overall yield for a one pot production of pure DNA minicircle is 30% (50 μg of a 95 bp minicircle produced per ml of circularization reaction with an initial amount of input DNA of 150 μg). Note that DNA minicircle purification can also be performed using silica bead DNA gel extraction kit according to the manual instructions (Thermo Scientific).

Production of Supercoiled DNA Minicircle Through the Formation of Nicked Circular Minicircle Intermediate:

The standard reaction of circularization can be used to produce nicked circular minicircle when an unphosphorylated 5' end is present on either strand of the overlapping duplex (FIG. 1B); in such a case, circularization reaction occurs by sealing DNA ends of one strand to form a minicircle containing a single nick in the other. The reaction mixture was then sequentially incubated with proteinase K (0.3 units, 30 min at 55° C.), T4 polynucleotide kinase with 1 mM ATP (200 units, 30 min at 37° C.) and finally with T4 DNA ligase (100 units, 1 h at 20° C.) in the absence or in the presence of increasing concentrations of ethidium bromide (Sigma-Aldrich) as indicated in the text. Ethidium bromide was then removed by butanol extraction. The purification steps were the same as described above and the overall yield of the reaction was 20%.

As shown in pathway 1 of FIG. 1B, the single nicked circular DNA was also treated with exonuclease III (3200 units, 2 h at 37° C.) allowing complete digestion of nicked strand to yield single-stranded minicircle which was then purified using silica bead DNA gel extraction kit (Thermo Scientific) (final yield of 10% as calculated from the starting double-stranded minicircle form); next, the single-stranded minicircle was allowed to hybridize in buffer containing 10 mM Tris-HCl, 25 mM NaCl, pH 7.5 with the complementary strand of 95 nt or with both complementary strands of 40 and 55 nt yielding respectively single-nicked minicircle or double-nicked minicircle.

Gel Electrophoresis Analysis:

Products formed in the circularization reaction were analyzed under native polyacrylamide gel electrophoresis. 130 ng of input DNA was loaded on a 5% native polyacrylamide gel (19:1, acrylamide:bisacrylamide (w/w), 90 mM Tris borate, 1 mM EDTA, pH 8.3) followed by migration at 12.5 V/cm for 90 min. After gel staining by SYBR Green (Invitrogen), the gel was imaged with a Typhoon Trio (GE Healthcare) and quantification of the gel bands was performed by ImageQuant software 5.1. Notice that in native polyacrylamide gel, the DNA was visualized by fluorescence and thus molar ratio of starting linear duplex over oligomers was calculated taking into account that band intensity is increased as a function of the oligomer length. Electrophoresis of minicircle was also performed as above with the additional presence of 10 mM $MgCl_2$ in order to separate minicircle topoisomers.

Minicircles generated in the circularization reaction were also analyzed on 8% denaturing polyacrylamide gel electrophoresis (19:1, acrylamide:bisacrylamide; 8 M urea; 90 mM Tris borate, 1 mM EDTA, pH 8.3); DNA samples in formamide were heat denaturated and 65 ng of DNA per sample was loaded on denaturating gel and electrophoresed at 18 Watts for 90 min. After gel staining by SYBR Green (Invitrogen), the gel was imaged with a Typhoon Trio (GE Healthcare) and quantification of the gel bands was performed by ImageQuant software 5.1.

Reaction of Fpg (8 units) with the 95 bp minicircle containing one or two 8-oxoguanine residues (0.2 µM) was carried out in buffer containing 50 mM NaCl, 25 mM Tris-HCl pH 7.6 for one hour at 37° C. After protein inactivation by heating at 60° C. during 10 min, the reaction products were analyzed on denaturating gel electrophoresis as indicated above.

Electrophoretic Mobility Shift Assay (EMSA)

EMSA was used for interaction studies of DNA minicircles with DNA binding proteins used herein. Abf2p was incubated with minicircle (10 ng) as a function of the concentration as indicated in the text in buffer containing 25 mM Tris-HCl, 100 mM NaCl, 1 mM DTT, 5% glycerol pH 7.6 for 10 min. After adding gel loading buffer, reaction mixture was loaded on a 5% native polyacrylamide gel (19:1, acrylamide:bisacrylamide (w/w); 90 mM Tris borate, 1 mM EDTA, pH 8.3). Gel was electrophoresed for 1 h. NF-κB p50/p50 was incubated with minicircle (10 ng) as a function of the concentration as indicated in the text in buffer containing 10 mM Tris-HCl, 50 mM NaCl, 3 mM DTT, 0.2 mM EDTA, 2% glycerol, 50 µg/ml acetylated BSA, pH 7.5 for 30 min at 4° C. After adding gel loading buffer, reaction mixture was loaded on a native 5% polyacrylamide gel (19:1, acrylamide:bisacrylamide (w/w); 90 mM Tris borate, 1 mM EDTA, pH 8.3). Gel was electrophoresed for 1 h. Streptavidin (Sigma-Aldrich) was incubated with DNA minicircle (10 ng) as a function of the concentration as indicated in the text with buffer containing 10 mM Tris-HCl, 50 mM NaCl, 3 mM DTT, 0.2 mM EDTA, 2% glycerol, 50 µg/ml acetylated BSA, pH 7.5. After addition of loading buffer, reaction mixture was loaded on a 5% polyacrylamide gel (19:1, acrylamide:bisacrylamide (w/w); 45 mM Tris borate, 0.5 mM EDTA, pH 8.3). Gel was electrophoresed for 1 h and staining was carried out by incubation of the gel in SYBR Green for 20 min. The gel was finally exposed to a Typhoon phosphoimager and the fraction bound (intensity of the bound complex/total intensity) was determined by ImageQuant 5.1 software.

Human Serum Stability of DNA Minicircle:

365 ng of DNA was incubated in 50% human serum (Sigma-Aldrich) at 37° C. Aliquots were taken as a function of time and immediately deproteinized twice by adding a mixture of phenol—chloroform-isoamyl alcohol (25:24:1) (Invitrogen). After centrifugation, an aliquot of the supernatant was loaded on agarose or polyacrylamide gel depending on the nature of nucleic acid incubated in serum (0.8% native agarose gel for plasmid DNA; 5% and 20% denaturating polyacrylamide gel for minicircle and linear DNA duplex, respectively). After electrophoresis, the gel was stained and the bands intensity quantified as described in section gel electrophoresis analysis. The band intensity corresponding to the starting nucleic acid of interest was reported as a function of incubation time. The data points were fitted to a single exponential. The rate constants of nucleic acids disappearance were used to deduce the half-time of nucleic acids stability in serum.

2—Results

DNA Minicircles Production:

The best commercially available chemical approach of oligonucleotide synthesis which is the solid-phase phosphoramidite method, enables production of single-stranded oligonucleotides in the range of 60 nucleotides (nt) with good yield and purity. Therefore, our method consisted in assembling appropriate overlapping oligonucleotides in order to form a starting blunt-ended DNA template of interest containing internal nicks (single-stranded cuts in one strand).

Figure 2:
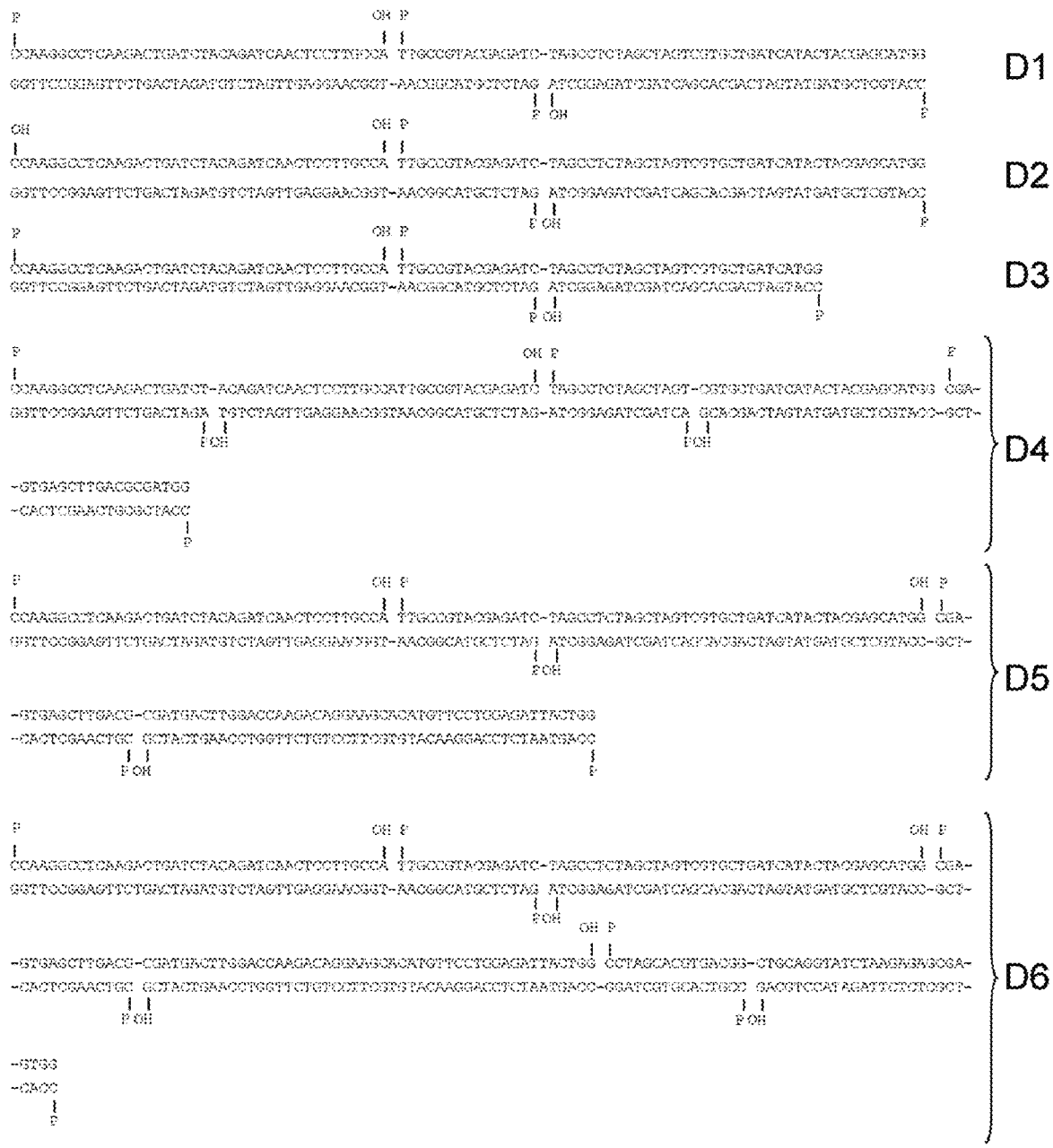
FIG. 2: Linear nicked blunt-ended duplexes D1 to D6, formed by hybridization of appropriate complementary oligonucleotides and used in the circularization method of the invention for minicircles production as depicted in FIG. 1. The sugar-phosphate backbone of both strands is nicked at the location indicated by the black arrow.

The linear nicked blunt-ended duplex of 95 bp was formed by mixing two appropriate overlapping oligonucleotides with two corresponding complementary oligonucleotides (FIG. 2, D1). All DNA 5' ends within D1 are phosphorylated in order to perform enzymatic ligation in the conditions as depicted below. Duplex D1 expectedly migrates on native polyacrylamide gel as one band with a mobility close to that of the 100 bp DNA fragment of the molecular weight marker. After incubation of D1 with T4 DNA ligase in the circularization buffer and in the absence of Abf2p, the starting band decreased and several intense bands of slower mobility appeared; as previously described in the literature, these bands correspond to linear oligomers of the starting D1 duplex, the most abundant oligomers being a dimer. This result demonstrates that at high DNA concentration such as used here (2 µM in duplex D1) only the contaminating intermolecular ligation products are formed without generation of minicircle from the nicked linear DNA substrate.

Conversely, when the same ligation reaction is carried out in the presence of the bending protein Abf2p, the reaction products are quite different. The band corresponding to the starting duplex D1 is very faint and an intense new band is present which corresponds to DNA minicircle; remarkably, all the bands corresponding to the contaminating linear oligomers have very weak intensity. The circularization efficiency can be roughly estimated by the ratio between the amount of minicircle over linear dimer; circularization with 95 bp DNA duplex D1 containing nicks yields a high ratio of 8 which is significantly less than ratio of 1.5 obtained in circularization reaction of continuous linear DNA substrate. Thus, our nicked DNA substrate is a very efficient input DNA for Abf2p-dependent induced flexibility over DNA duplex with continuity of the sugar-phosphate backbone. The introduction of a nick in each strand separated by an overlapping sequence of 15 base pairs is a relevant finding contributing to high yield of minicircle production at elevated DNA concentration. The DNA flexibility introduced by the presence of strand nicks is deduced from the fact that Abf2p exhibits similar high binding affinity for linear nicked DNA substrate as compared to the corresponding DNA minicircle, such circular DNA form being well known preferential DNA substrate for Abf2p. Parameters such as the nature of the base pairs flanking the nicks, the length and position of the overlapping sequence, the ligase amount could have a bearing on the efficiency of the circularization reaction. Several combinations of these parameters modulate poorly the circularization reaction. Notably, we found that the yield of the reaction was independent of the length of the overlapping region; indeed, overlapping of 10, 15 and 20 base pairs did not contribute to modulation of the reaction efficiency indicating that nicks induce DNA flexibility that improves efficiency of Abf2p to bind and likely bend DNA for efficient ligase-mediated DNA circularization reaction.

The mixture is subsequently treated with T5 exonuclease; such enzyme digested efficiently linear double-stranded DNA from 5'-end and exhibits a weaker endonuclease activity with single-stranded DNA. Following ethanol precipitation and gel loading, all linear forms of DNA have been digested by the enzyme on the contrary to the double-stranded closed circular minicircle which is resistant to exonuclease digestion in the absence of free ends as expected. Because the size of circular DNA cannot be established from gel electrophoresis, we next verified that the minicircle product can give back a starting linear 95 bp duplex by taking advantage of the presence of a single HaeIII restriction site specifically formed during the circularization reaction; after incubation of the minicircle with HaeIII, the migration is the same as that of the 95 bp linear duplex showing that the starting product is a 95 bp minicircle. The overall yield for a one pot production of pure DNA minicircle is 30% (50 μg of a 95 bp minicircle produced per ml of circularization reaction with an initial amount of input DNA of 150 μg).

To make sure that minicircles were free of nicks following T5 exonuclease activity (covalently closed minicircles), the final 95 bp minicircle was electrophoresed on a denaturating polyacrylamide gel; DNA minicircle migrates as one band suggesting that it is entirely covalently closed. To control that nicked minicircle intermediates were readily separated on gel under denaturating conditions, we constructed two nicked minicircles intermediates. For that purpose, we used a starting linear DNA (FIG. 2, D2) for which only one 5' end is phosphorylated on either strand in order for circularization to take place by sealing DNA ends of only one strand (FIG. 1B); digestion of the nicked strand of the minicircle yields single-stranded DNA minicircle (FIG. 1B, pathway 1); equimolar hybridization with the complementary single-stranded ODN of 95 nucleotides (nt) or with both complementary 40 and 55 nt single-stranded oligonucleotides results in the formation of single and double nicked minicircles, respectively. Each nicked circular DNA control migrates as several bands on the denaturating gel: single-stranded oligonucleotides and single-stranded minicircle. This experiment shows that double-stranded DNA minicircle produced by our methodology is devoid of nicked strands.

As shown in FIG. 1B (pathway 1), our method can also be used easily for the preparation of single-stranded circular minicircles with similar yield as for double-stranded minicircle production. Thus our method is of interest to construct both circular double- and single-stranded DNA nano-objects.

Abf2p has been shown to introduce negative superhelical turns in plasmid through DNA unwinding. To determine whether the minicircle produced in our method is supercoiled or not we used two standard methods, i.e. native gel electrophoresis and sensitivity to the nuclease Bal31. It is known that the presence of magnesium counterions in polyacrylamide gel electrophoresis helps to separate DNA minicircle as a function of the extent of negative supercoiling. 95 bp single nicked minicircle prepared as depicted in pathway 1 of FIG. 1B, is used as control for unconstraint DNA. DNA minicircle prepared in our standard method with Abf2p/DNA molar ratio of 1 (this ratio being defined as the concentration of Abf2p in mole/l over the concentration of DNA duplex in mole/l) exhibits the same migration as that of nicked DNA minicircle; this result suggests that 95 bp minicircle produced here is relaxed covalently closed circular DNA. To confirm this data, the minicircle was incubated with Bal31 nuclease in conditions that were previously used to digest constrained but not relaxed DNA minicircle. The DNA minicircle produced in our methodology is resistant to Bal31 confirming the formation of relaxed closed circular DNA and showing that the presence of Abf2p does not induce DNA unwinding in our assay conditions. Note that 95 bp minicircle has an integral number of helical repeats ($Lk_0$) equal to 9 (95 bp divided by 10.54 bp) assuming that helical repeat of the DNA minicircle is 10.54 bp/turn under our experimental conditions. Hence covalent closure of the duplex occurs without twisting.

The present strategy can yield minicircles of various sizes depending on the length of the input starting linear overlapping duplex D3, D4, D5 and D6 as shown in FIG. 2. Thus minicircles of 84, 95, 116, 158 and 200 bp in length have been produced successfully.

Figure 3:
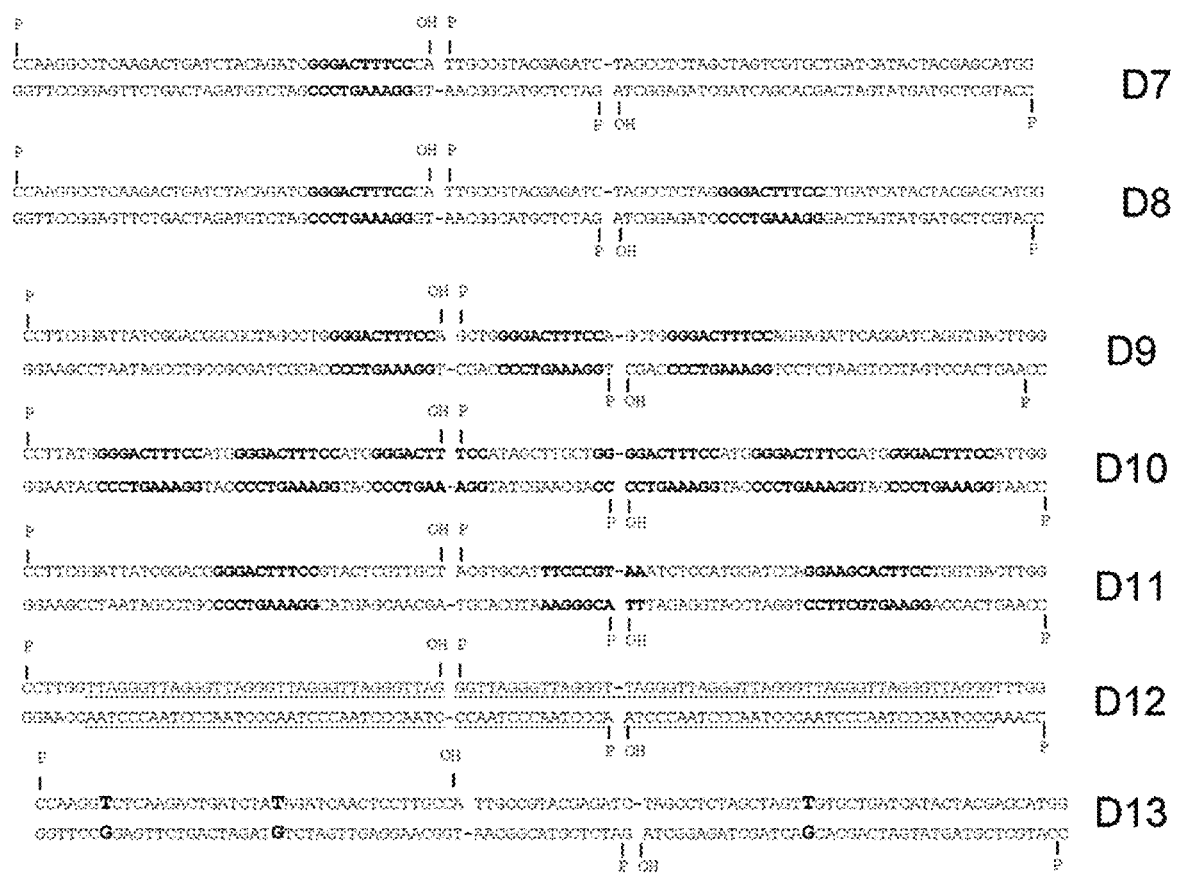
Figure 5:
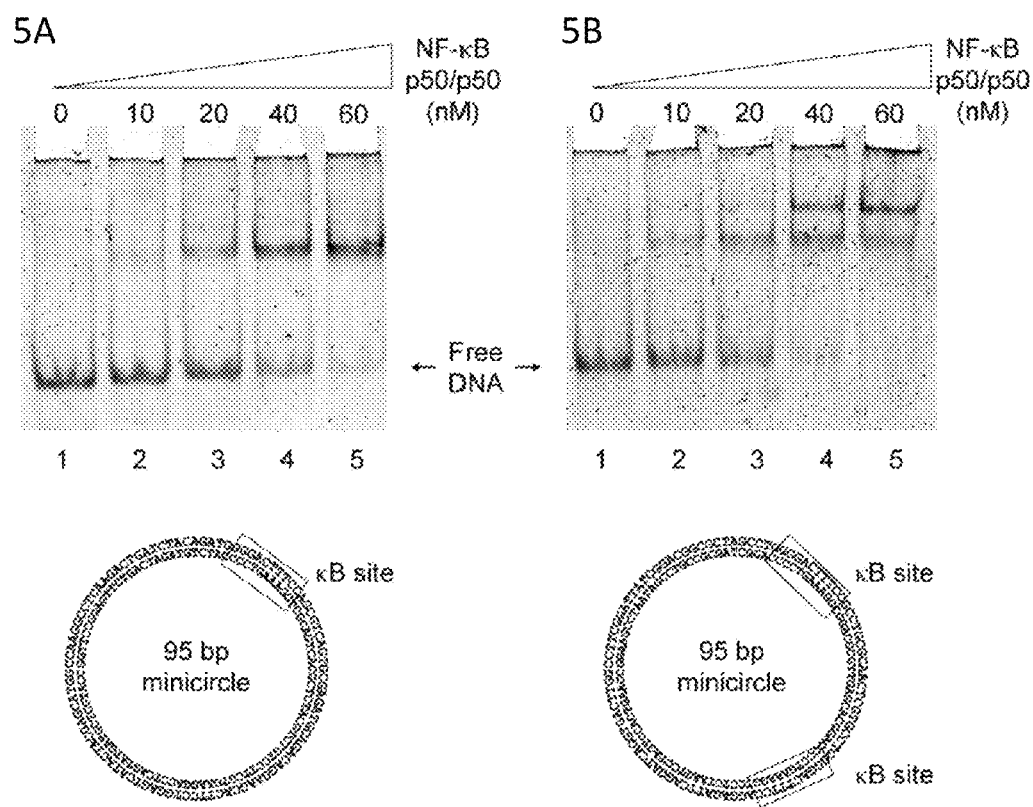
FIG. 5: 95 bp relaxed DNA minicircle designed to include one (A) or two (B) NF-κB binding sequences is capable to interact respectively with one or two NF-κB proteins as shown by EMSA.

Freedom to Choose the Nature and Position of DNA Sequences Present in a DNA Minicircle (FIG. 3):

The data reported above were obtained with DNA containing random sequence. To exemplify the versatility of our method regarding the nature and position of DNA sequence used to form minicircles, the applicant has next designed DNA minicircle containing consensus sequences for the well-known transcription factor NF-κB (FIG. 3). The 95 bp minicircles containing one or two κB binding sites (GGGACTTTCC) were generated in the same conditions as depicted above (FIG. 3, D7 and D8). The yield of the reaction was unchanged and independent of the position of the κB sequence (in the overlapping region or at the ends of the starting linear nicked DNA). The binding capacity of such DNA minicircles was next tested according to the number of binding site. Electrophoretic mobility shift assay (EMSA) was performed using non labeled DNA minicircles and SYBR green staining which presents the advantage to avoid radioactive labeling thanks to the high amount of minicircles produced by the present method. Example of binding activity of NF-κB with minicircles is shown in FIG. 5. First, a relaxed closed minicircle of 95 bp containing a single NF-κB binding site (FIG. 5, A) was incubated with increasing concentration of NF-κB and then the reaction mixture was analyzed by EMSA. In the presence of NF-κB protein (p50/p50 homodimer), a retarded band is observed corresponding to the DNA protein complex the intensity of which is increased as a function of protein concentration. When a second binding site is present within the minicircle, we observed the presence of a second more slowly retarded band corresponding to the binding of a second protein to the minicircle (FIG. 5, B). This result shows that short DNA minicircles are capable to attract efficiently DNA binding proteins such as a transcription factor. NF-κB is implicated in cancer through inflammatory pathways stimulation. The capability of minicircle to attract specifically target proteins of therapeutic interest is of great interest for therapeutic applications (decoy strategy).

95 bp minicircles encompassing several NF-κB sequences such as the sequence 3NF previously used for enhancement of plasmid DNA nuclear import or a sequence of 6 κB sequences (starting duplexes D9 and D10 as shown in FIG. 3); a 95 bp minicircle with a combination of various transcription factor binding sites (NF-κB, ETS1, STAT3) was also produced efficiently using the starting duplex D11.

Human telomeric sequence (TTAGGG) can also be part of a 95 bp minicircle using duplex D12; DNA mismatches can also be introduced within minicircles using duplex D13 showing that the method presented here enables preparation of minicircles with DNA distortions.

Thus the overall yield of minicircles production with various sequences as presented herein, is mainly dependent on the presence of nicks in the starting DNA substrates to be circularized together on Abf2p activity. However, we cannot completely rule out that the efficiency of circularization reaction could be modulated by unforeseen DNA sequence effect. In such a case, it is advised to control the annealing of oligonucleotides by simple analysis of duplexes on a native polyacrylamide gel electrophoresis and/or to increase the amount of Abf2p in the circularization reaction.

Production of Minicircles Containing Chemical Functionalities (FIG. 4):

Commercially available synthetic DNA oligonucleotides are easily functionalized with various base analogs and modifications in the course of solid support synthesis. Here we extended our methodology of circularization to DNA containing several base modifications in order to know whether circularization reaction is permissive for chemically modified oligonucleotides Minicircle with Site-Specifically Placed Natural Base Modification:

8-oxoguanine:

8-oxoguanine is a base modification formed naturally when DNA is subjected to oxidative conditions or ionizing radiations. Such lesion can be repaired by the well-known *E. coli*-derived formamidopyrimidine (Fpg) repair protein which catalyzes the excision of 8-oxoguanine yielding a strand nick in the present assay.

Figure 4:
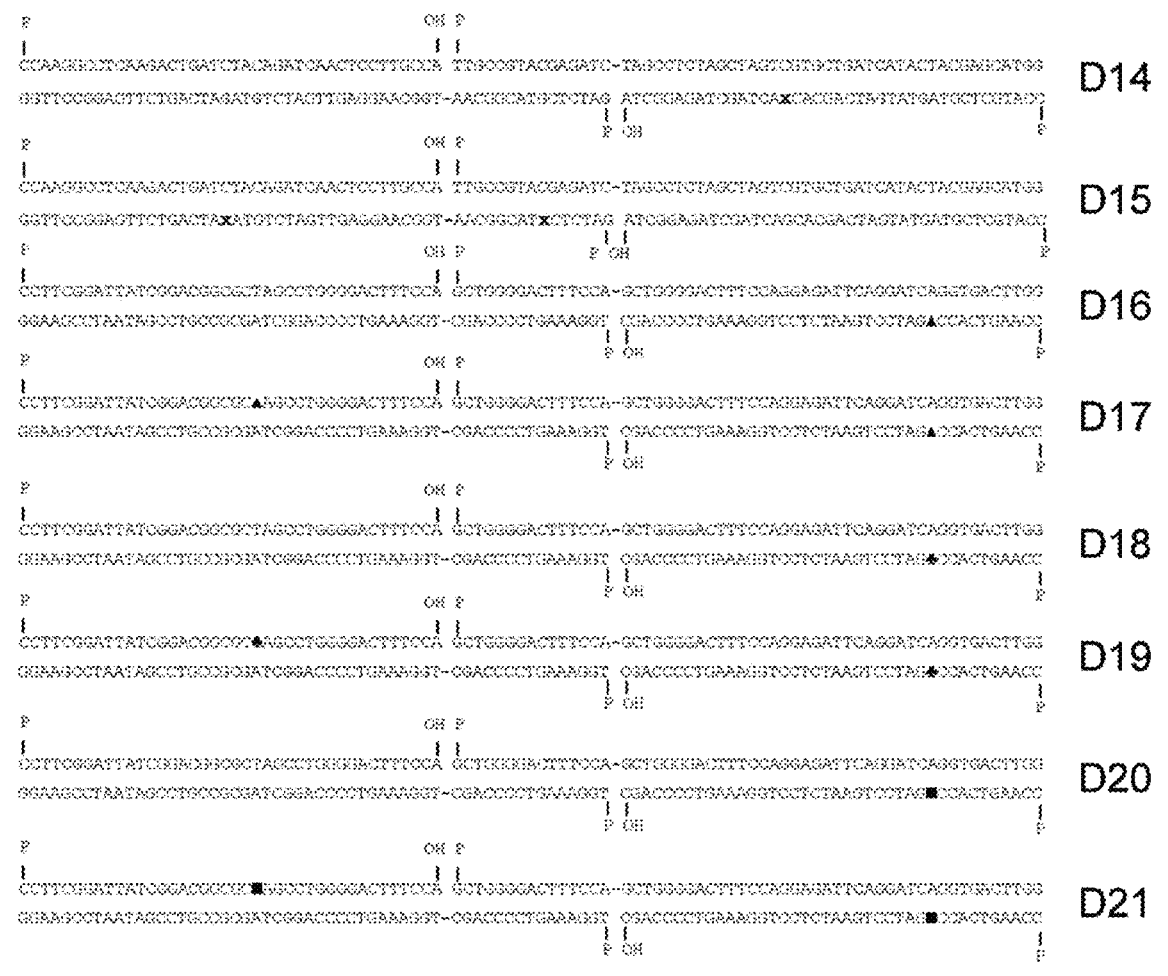

95 bp minicircles were produced from input DNA containing either one or two 8-oxoguanine residues within the same strand (FIG. 4, D14, D15). The production yield of single or double 8-oxoguanine-modified minicircles was insensitive to the presence of base modification within DNA and the 95 bp minicircle with or without base modification migrates identically as a single band on denaturating PAGE; when the minicircle containing a single base modification is incubated in the presence of Fpg and then the reaction mixture is loaded on denaturating gel, one can observed that the starting band corresponding to the minicircle disappeared to give rise to two new bands, co-migrating respectively as a single-stranded minicircle of 95 nt and a linear fragment of 94 nt. Introducing two 8-oxoguanine residues within the same strand of a 95 bp minicircle at position as indicated (FIG. 4, D15) yields the expected size of DNA products following Fpg activity. The capability of DNA minicircle bearing several modified bases to attract and to be substrate for repair proteins of therapeutic interest is of great interest for biological applications (decoy based strategy).

Our methodology can be extended to incorporate a variety of modified bases within DNA minicircle with the purpose to trap several target proteins implicated in cancer: repair proteins such as O6-alkylguanine-DNA alkyltransferase with 06-Me-dG modified base; DNA methyltransferase such as cytosine-5 methyltransferase with methylated cytosine modified base.

DNA Minicircles with Site-Specifically Placed Labels:
Biotin Residues

We first investigated whether the presence of a derivative dT nucleotide with a biotin molecule linked by a spacer to the C5-atom of pyrimidin ring could modulate or not the circularization reaction used in our methodology. After completion of our protocol using duplex D16 (FIG. 4), we obtained pure closed DNA minicircle without decrease in the yield of production. The minicircle with and without a biotin residue migrated as a single band at the bottom of the EMSA gel. When minicircles are pre incubated with streptavidin, a slower migrating band is observed only when the minicircle contains a biotin residue showing that streptavidin binds biotin-labeled minicircle. A second biotin can also be incorporated when placed on the opposite DNA strand (FIG. 4, D17); therefore, Abf2p-dependent circularization reaction supports the presence of bulky DNA modifications.

Fluorophores:

Because biotin itself is a relatively small residue, we next investigated whether a larger molecule such as fluorophore could be used as label in place of biotin. Using input cyanine 3 or carboxyfluorescein modified-DNA (FIG. 4, D18, D19, D20, D21) our methodology generates in good amount 95 bp minicircle site-specifically labeled by cyanine 3 or carboxyfluorescein; as deduced from spectrophotometry measurement, the ratio of fluorophore over nucleotide confirmed that one or two fluorophores are present per minicircle.

Figure 6:
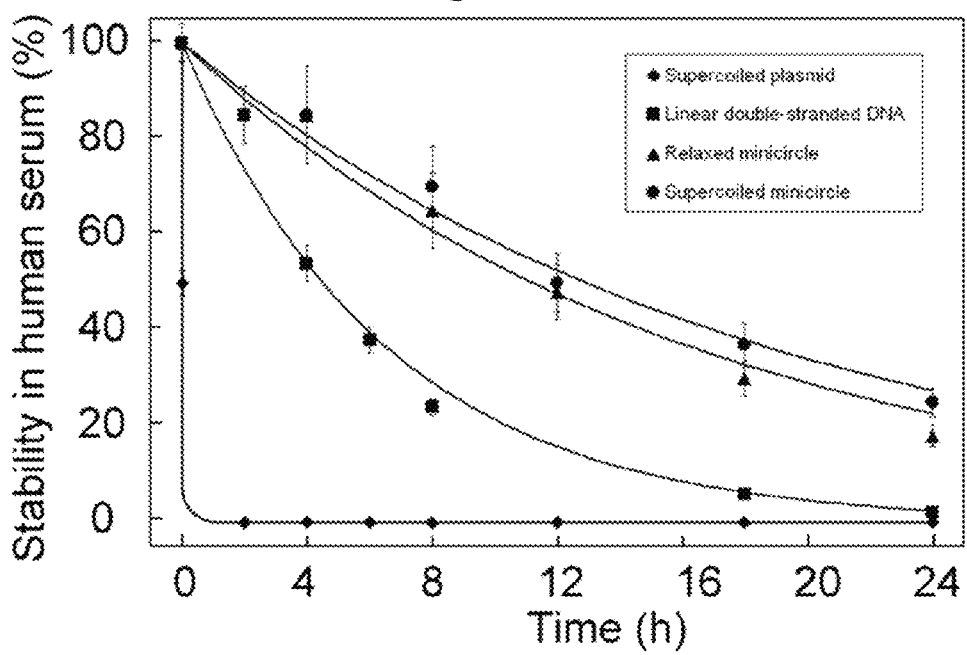
FIG. 6: Minicircle stability in human serum: nucleic acids were incubated with human serum as a function of time at 37° C. Each time point corresponds to the amount of starting nucleic acids as analyzed by gel electrophoresis. The curves represent the fit to a single exponential. Data points and error bars represent the average and standard deviation (respectively) from at least three experiments (diamonds: supercoiled plasmid; squares: linear double-stranded DNA, triangles: relaxed minicircle; circles: supercoiled minicircles).

Resistance to Nuclease Activity in Serum (FIG. 6):

As illustrated in the experiments and results shown above, closed double-stranded minicircles of the present invention are resistant to recombinant exonuclease proteins, such as exonuclease 1111 and T5 exonuclease. It is known that exonuclease activity is the main mechanism of exogenous DNA degradation in cell cytoplasm rather than endonuclease activity (Sasaki, A. and Kinjo., M., 2010, J. Control. Release 143, 104-111). It is therefore anticipated that minicircle should have high stability in cell. However, an important limiting step in the use of nucleic acids in molecular therapy such as the decoy strategy is the great instability in blood. To determine DNA minicircle sensitivity to nuclease degradation, we incubated DNA minicircle in human serum at 37° C. Aliquots were taken as a function of time and minicircle stability analyzed after migration on polyacrylamide gel. The amount of starting minicircle was quantified as a function of time as shown in FIG. 6. The half-life of 95 bp minicircles was found to be about 11 and 13 hours for relaxed and constrained form, respectively. For purpose comparison, we found that a supercoiled plasmid DNA showed a very short half-life of about one minute in our experimental conditions, in agreement with previous data (Houk, B. E. et al., 1999, AAPS Pharmsci. 1, 1-5). Also in agreement with the literature (Osako, M., K. et al., 2007, J. Gene Med. 9, 812-819), linear DNA duplex was found to be very susceptible to serum nuclease degradation. Thus minicircle with a phosphodiester backbone according to the invention exhibits a high stability in human serum at 37° C. which is a required property for further use of minicircle as therapeutic oligonucleotide.

Figure 7:
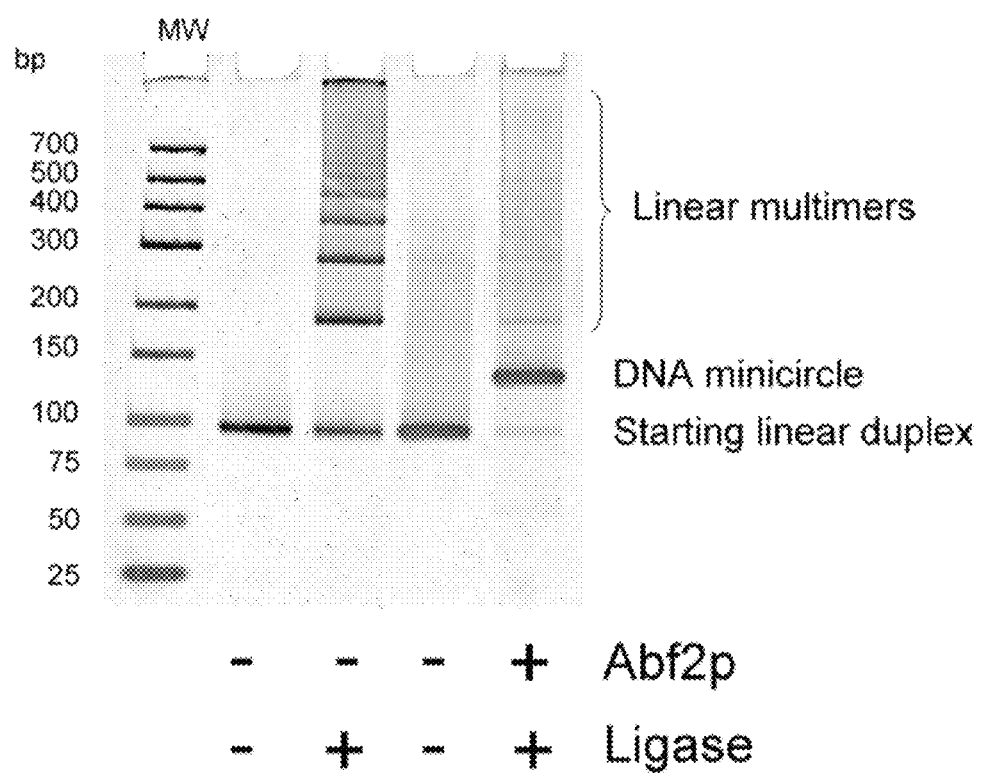
FIG. 7: Image of a stained native polycrylamide gel, presenting the electrophoretic run of various DNA samples. Lane 1: commercial molecular weight (MW) marker; lane 2: 95 bp linear DNA duplex; lane 3: 95 bp DNA duplex after one hour incubation with T4 DNA ligase at 20° C.; lane 4: 95 bp nicked linear DNA duplex; lane 5: 95 bp nicked DNA duplex after one hour incubation with T4 DNA ligase and the bending protein Abf2p at 20° C. The nature of the components corresponding to the different bands is indicated on the right.

Comparative Results (FIG. 7):

The method for obtaining DNA minicircles of the invention has been compared to experimental conditions used in the prior art for obtaining minicircles, notably to a ligase-mediated circularization method using linear non-nicked DNA duplex as substrate and without the use of a bending protein during the circularization reaction. FIG. 7 shows an image of stained native polyacrylamide gel illustrating the strong decrease of oligomeric linear products formed in ligase-mediated circularization with the concomitant formation of minicircle product in the presence of Abf2p bending protein as compared to reaction carried out in the absence of Abf2p. The ligase used is the T4 DNA ligase. Incubation of the DNA duplex with the ligase has been performed with (line 5) or without (line 2) Abf2p.

These results demonstrate that in the experimental conditions of the prior art (i.e.: using non-nicked DNA substrate and without DNA bending protein), the T4 DNA ligase is completely unable to generate circular DNA from a linear duplex of 95 bp (see lane 3 of FIG. 7). The ligation products formed in such a reaction are linear multimers and importantly no DNA minicircle is formed. For purpose comparison is shown in lane 5 a typical reaction condition as depicted in the present invention showing the formation with high yield of a DNA minicircle with a faint amount of linear multimers. These data illustrate that small DNA fragments are completely resistant to ligase-mediated circularization.

These results demonstrate that the combined use of linear synthetic nicked substrates and of a DNA bending protein during the ligase-dependent cyclization step drastically improves the yield of the production of minicircles of any size (even below 250 base pairs). Such method also provides a great flexibility in the design of minicircles of any size and sequence and encompassing base modifications.

SEQUENCE LISTING

<160> NUMBER OF SEQ ID NOS: 21

<210> SEQ ID NO 1
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="linear nicked blunt-ended duplex"
      /organism="Artificial Sequence"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"

<400> SEQUENCE: 1
ccaaggcctc aagactgatc tacagatcaa ctccttgcca ttgccgtacg agatctagcc    60
tctagctagt cgtgctgatc atactacgag catgg                              95

<210> SEQ ID NO 2
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="linear nicked blunt-ended duplex"
      /organism="Artificial Sequence"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"

```
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"

<400> SEQUENCE: 2
gcctcaacca aggactgatc tacagatcaa ctccttgcca ttgccgtacg agatctagcc    60
tctagctagt cgtgctgatc atactacgag catgg                              95

<210> SEQ ID NO 3
<211> LENGTH: 84
<212> TYPE: DNA
<213> ORGANISM: Artificial Sequence
<220> FEATURE:
<221> NAME/KEY: source
<222> LOCATION: 1..84
<223> OTHER INFORMATION: /mol_type="unassigned DNA"
      /note="linear nicked blunt-ended duplex"
      /organism="Artificial Sequence"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: complement(84)
<223> OTHER INFORMATION: /note="A phosphate group is attached to the 5'
      carbon in the sugar-ring of the deoxyribose of nucleotide 84 of
      complementary strand"

<400> SEQUENCE: 3
ccaaggcctc aagactgatc tacagatcaa ctccttgcca ttgccgtacg agatctagcc    60
```

```
tctagctagt cgtgctgatc atgg                                           84
```

```
<210> SEQ ID NO 4
<211> LENGTH: 116
<212> TYPE: DNA
<213> ORGANISM: Artificial Sequence
<220> FEATURE:
<221> NAME/KEY: source
<222> LOCATION: 1..116
<223> OTHER INFORMATION: /mol_type="unassigned DNA"
     /note="linear nicked blunt-ended duplex"
     /organism="Artificial Sequence"
<220> FEATURE:
<221> NAME/KEY: misc_feature
<222> LOCATION: 1
<223> OTHER INFORMATION: /note="A phosphate group is attached to the 5'
     carbon in the sugar-ring of the deoxyribose of nucleotide 1"
<220> FEATURE:
<221> NAME/KEY: misc_feature
<222> LOCATION: complement(21)
<223> OTHER INFORMATION: /note="A phosphate group is attached to the 5'
     carbon in the sugar-ring of the deoxyribose of nucleotide 21 of
     complementary strand"
<220> FEATURE:
<221> NAME/KEY: misc_feature
<222> LOCATION: complement(21^22)
<223> OTHER INFORMATION: /note="Presence of a nick (no phosphodiester
     bond) between adjacent nucleotides 21 and 22 of complementary
     strand"
<220> FEATURE:
<221> NAME/KEY: misc_feature
<222> LOCATION: 55^56
<223> OTHER INFORMATION: /note="Presence of a nick (no phosphodiester
     bond) between adjacent nucleotides 55 and 56"
<220> FEATURE:
<221> NAME/KEY: misc_feature
<222> LOCATION: 56
<223> OTHER INFORMATION: /note="A phosphate group is attached to the 5'
     carbon in the sugar-ring of the deoxyribose of nucleotide 56"
<220> FEATURE:
<221> NAME/KEY: misc_feature
<222> LOCATION: complement(70)
<223> OTHER INFORMATION: /note="A phosphate group is attached to the 5'
     carbon in the sugar-ring of the deoxyribose of nucleotide 70 of
     complementary strand"
<220> FEATURE:
<221> NAME/KEY: misc_feature
<222> LOCATION: complement(70^71)
<223> OTHER INFORMATION: /note="Presence of a nick (no phosphodiester
     bond) between adjacent nucleotides 70 and 71 of complementary
     strand"
<220> FEATURE:
<221> NAME/KEY: misc_feature
<222> LOCATION: 95^96
<223> OTHER INFORMATION: /note="Presence of a nick (no phosphodiester
     bond) between adjacent nucleotides 95 and 96"
<220> FEATURE:
<221> NAME/KEY: misc_feature
<222> LOCATION: 96
<223> OTHER INFORMATION: /note="A phosphate group is attached to the 5'
     carbon in the sugar-ring of the deoxyribose of nucleotide 96"
<220> FEATURE:
<221> NAME/KEY: misc_feature
<222> LOCATION: complement(116)
<223> OTHER INFORMATION: /note="A phosphate group is attached to the 5'
     carbon in the sugar-ring of the deoxyribose of nucleotide 116 of
     complementary strand"

<400> SEQUENCE: 4
ccaaggcctc aagactgatc tacagatcaa ctccttgcca ttgccgtacg agatctagcc    60
tctagctagt cgtgctgatc atactacgag catggcgagt gagcttgacg cgatgg       116

<210> SEQ ID NO 5
<211> LENGTH: 158
<212> TYPE: DNA
```

```
<213> ORGANISM: Artificial Sequence
<220> FEATURE:
<221> NAME/KEY: source
<222> LOCATION: 1..158
<223> OTHER INFORMATION: /mol_type="unassigned DNA"
      /note="linear nicked blunt-ended duplex"
      /organism="Artificial Sequence"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: 55^56
<223> OTHER INFORMATION: /note="A phosphate group is attached to the 5'
      carbon in the sugar-ring of the deoxyribose of nucleotide 55 and
      56 of complementary strand"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: 96
<223> OTHER INFORMATION: /note="A phosphate group is attached to the 5'
      carbon in the sugar-ring of the deoxyribose of nucleotide 96"
<220> FEATURE:
<221> NAME/KEY: misc_feature
<222> LOCATION: 95^96
<223> OTHER INFORMATION: /note="Presence of a nick (no phosphodiester
      bond) between adjacent nucleotides 95 and 96"
<220> FEATURE:
<221> NAME/KEY: misc_feature
<222> LOCATION: complement(110^111)
<223> OTHER INFORMATION: /note="Presence of a nick (no phosphodiester
      bond) between adjacent nucleotides 110 and 111 of complementary
      strand"
<220> FEATURE:
<221> NAME/KEY: misc_feature
<222> LOCATION: complement(158)
<223> OTHER INFORMATION: /note="A phosphate group is attached to the 5'
      carbon in the sugar-ring of the deoxyribose of nucleotide 158 of
      complementary strand"
<220> FEATURE:
<221> NAME/KEY: misc_feature
<222> LOCATION: complement(110)
<223> OTHER INFORMATION: /note="A phosphate group is attached to the 5'
      carbon in the sugar-ring of the deoxyribose of nucleotide 110 of
      complementary strand"

<400> SEQUENCE: 5
ccaaggcctc aagactgatc tacagatcaa ctccttgcca ttgccgtacg agatctagcc      60
tctagctagt cgtgctgatc atactacgag catggcgagt gagcttgacg cgatgacttg     120
gaccaagaca ggaagcacat gttcctggag attactgg                             158

<210> SEQ ID NO 6
<211> LENGTH: 199
<212> TYPE: DNA
<213> ORGANISM: Artificial Sequence
<220> FEATURE:
<221> NAME/KEY: source
<222> LOCATION: 1..199
```

```
<223> OTHER INFORMATION: /mol_type="unassigned DNA"
     /note="Linear nicked blunt-ended suplex"
     /organism="Artificial Sequence"
<220> FEATURE:
<221> NAME/KEY: misc_feature
<222> LOCATION: 1
<223> OTHER INFORMATION: /note="A phosphate group is attached to the 5'
     carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
     carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
     carbon in the sugar-ring of the deoxyribose of nucleotide 55 of
     complementary strand"
<220> FEATURE:
<221> NAME/KEY: misc_feature
<222> LOCATION: 96
<223> OTHER INFORMATION: /note="A phosphate group is attached to the 5'
     carbon in the sugar-ring of the deoxyribose of nucleotide 96"
<220> FEATURE:
<221> NAME/KEY: misc_feature
<222> LOCATION: 159
<223> OTHER INFORMATION: /note="A phosphate group is attached to the 5'
     carbon in the sugar-ring of the deoxyribose of nucleotide 159"
<220> FEATURE:
<221> NAME/KEY: misc_feature
<222> LOCATION: complement(173)
<223> OTHER INFORMATION: /note="A phosphate group is attached to the 5'
     carbon in the sugar-ring of the deoxyribose of nucleotide 173 of
     complementary strand"
<220> FEATURE:
<221> NAME/KEY: misc_feature
<222> LOCATION: complement(110)
<223> OTHER INFORMATION: /note="A phosphate group is attached to the 5'
     carbon in the sugar-ring of the deoxyribose of nucleotide 110 of
     complementary strand"
<220> FEATURE:
<221> NAME/KEY: misc_feature
<222> LOCATION: complement(199)
<223> OTHER INFORMATION: /note="A phosphate group is attached to the 5'
     carbon in the sugar-ring of the deoxyribose of nucleotide 199 of
     complementary strand"
<220> FEATURE:
<221> NAME/KEY: misc_feature
<222> LOCATION: 40^41
<223> OTHER INFORMATION: /note="Presence of a nick (no phosphodiester
     bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
     bond) between adjacent nucleotides 55 and 56 of complementary
     strand"
<220> FEATURE:
<221> NAME/KEY: misc_feature
<222> LOCATION: 95^96
<223> OTHER INFORMATION: /note="Presence of a nick (no phosphodiester
     bond) between adjacent nucleotides 95 and 96"
<220> FEATURE:
<221> NAME/KEY: misc_feature
<222> LOCATION: complement(110^111)
<223> OTHER INFORMATION: /note="Presence of a nick (no phosphodiester
     bond) between adjacent nucleotides 110 and 111 of complementary
     strand"
<220> FEATURE:
<221> NAME/KEY: misc_feature
<222> LOCATION: 158^159
<223> OTHER INFORMATION: /note="Presence of a nick (no phosphodiester
     bond) between adjacent nucleotides 158 and 159"
<220> FEATURE:
<221> NAME/KEY: misc_feature
<222> LOCATION: complement(173^174)
<223> OTHER INFORMATION: /note="Presence of a nick (no phosphodiester
     bond) between adjacent nucleotides 173 and 174 of complementary
``` strand"

<400> SEQUENCE: 6
ccaaggcctc aagactgatc tacagatcaa ctccttgcca ttgccgtacg agatctagcc    60
tctagctagt cgtgctgatc atactacgag catggcgagt gagcttgacg cgatgacttg   120
gaccaagaca ggaagcacat gttcctggag attactggcc tagcacgtga cggctgcagg   180
tatctaagag agcgagtgg                                                199

<210> SEQ ID NO 7
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="Linear nicked blunt-ended duplex"
      /organism="Artificial Sequence"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"
<220> FEATURE:
<221> NAME/KEY: misc_feature
<222> LOCATION: 29..38
<223> OTHER INFORMATION: /note="Consensus sequence for NF kappa B
      transcription factor from nucleotide 29 to nucleotide 38"

<400> SEQUENCE: 7
ccaaggcctc aagactgatc tacagatcgg gactttccca ttgccgtacg agatctagcc    60
tctagctagt cgtgctgatc atactacgag catgg                               95

<210> SEQ ID NO 8
<211> LENGTH: 96
<212> TYPE: DNA
<213> ORGANISM: Artificial Sequence
<220> FEATURE:
<221> NAME/KEY: source
<222> LOCATION: 1..96
<223> OTHER INFORMATION: /mol_type="unassigned DNA"
      /note="linear nicked blunt-ended duplex"
      /organism="Artificial Sequence"

```
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: 29..38
<223> OTHER INFORMATION: /note="Consensus sequence for NF kappa B
      transcription factor from nucleotide 29 to nucleotide 38"
<220> FEATURE:
<221> NAME/KEY: misc_feature
<222> LOCATION: 66..75
<223> OTHER INFORMATION: /note="Consensus sequence for NF kappa B
      transcription factor from nucleotide 66 to nucleotide 75"

<400> SEQUENCE: 8
ccaaggcctc aagactgatc tacagatcgg gactttccca ttgccgtacg agatctagcc      60
tctaggggac tttccctgat catactacga gcatgg                                96

<210> SEQ ID NO 9
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="Linear nicked blunt-ended duplex"
      /organism="Artificial Sequence"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
```

<222> LOCATION: complement(95)
<223> OTHER INFORMATION: /note="A phosphate group is attached to the 5'
     carbon in the sugar-ring of the deoxyribose of nucleotide 95 of
     complementary strand"
<220> FEATURE:
<221> NAME/KEY: misc_feature
<222> LOCATION: 40^41
<223> OTHER INFORMATION: /note="Presence of a nick (no phosphodiester
     bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
     bond) between adjacent nucleotides 55 and 56 of complementary
     strand"
<220> FEATURE:
<221> NAME/KEY: misc_feature
<222> LOCATION: 30..39
<223> OTHER INFORMATION: /note="Consensus sequence for NF kappa B
     transcription factor from nucleotide 30 to nucleotide 39"
<220> FEATURE:
<221> NAME/KEY: misc_feature
<222> LOCATION: 45..54
<223> OTHER INFORMATION: /note="Consensus sequence for NF kappa B
     transcription factor from nucleotide 45 to nucleotide 54"
<220> FEATURE:
<221> NAME/KEY: misc_feature
<222> LOCATION: 60..69
<223> OTHER INFORMATION: /note="Consensus sequence for NF kappa B
     transcription factor from nucleotide 60 to nucleotide 69"

<400> SEQUENCE: 9
ccttcggatt atcggacggc gctagcctgg ggactttcca gctggggact ttccagctgg    60
ggactttcca ggagattcag gatcaggtga cttgg                              95

<210> SEQ ID NO 10
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
     /note="Linear nicked blunt-ended sequence"
     /organism="Artificial Sequence"
<220> FEATURE:
<221> NAME/KEY: misc_feature
<222> LOCATION: 1
<223> OTHER INFORMATION: /note="A phosphate group is attached to the 5'
     carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
     carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
     carbon in the sugar-ring of the deoxyribose of nucleotide 55 of
     complementary strand"
<220> FEATURE:
<221> NAME/KEY: misc_feature
<222> LOCATION: complement(95)
<223> OTHER INFORMATION: /note="A phosphate group is attached to the 5'
     carbon in the sugar-ring of the deoxyribose of nucleotide 95 of
     complementary strand"
<220> FEATURE:
<221> NAME/KEY: misc_feature
<222> LOCATION: 40^41
<223> OTHER INFORMATION: /note="Presence of a nick (no phosphodiester
     bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester

```
        bond) between adjacent nucleotides 55 and 56 of complementary
        strand"
<220> FEATURE:
<221> NAME/KEY: misc_feature
<222> LOCATION: 8..17
<223> OTHER INFORMATION: /note="Consensus sequence for NF kappa B
        transcription factor from nucleotide 8 to nucleotide 17"
<220> FEATURE:
<221> NAME/KEY: misc_feature
<222> LOCATION: 21..30
<223> OTHER INFORMATION: /note="Consensus sequence for NF kappa B
        transcription factor from nucleotide 21 to nucleotide 30"
<220> FEATURE:
<221> NAME/KEY: misc_feature
<222> LOCATION: 34..43
<223> OTHER INFORMATION: /note="Consensus sequence for NF kappa B
        transcription factor from nucleotide 34 to nucleotide 43"
<220> FEATURE:
<221> NAME/KEY: misc_feature
<222> LOCATION: 54..64
<223> OTHER INFORMATION: /note="Consensus sequence for NF kappa B
        transcription factor from nucleotide 54 to nucleotide 64"
<220> FEATURE:
<221> NAME/KEY: misc_feature
<222> LOCATION: 68..77
<223> OTHER INFORMATION: /note="Consensus sequence for NF kappa B
        transcription factor from nucleotide 68 to nucleotide 77"
<220> FEATURE:
<221> NAME/KEY: misc_feature
<222> LOCATION: 81..90
<223> OTHER INFORMATION: /note="Consensus sequence for NF kappa B
        transcription factor from nucleotide 81 to nucleotide 90"

<400> SEQUENCE: 10
ccttatgggg actttccatg gggactttcc atggggactt tccatagctt gctggggact      60
ttccatgggg actttccatg gggactttcc attgg                                 95

<210> SEQ ID NO 11
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
        /note="Liner nicked blunt-ended duplex"
        /organism="Artificial Sequence"
<220> FEATURE:
<221> NAME/KEY: misc_feature
<222> LOCATION: 1
<223> OTHER INFORMATION: /note="A phosphate group is attached to the 5'
        carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
        carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
        carbon in the sugar-ring of the deoxyribose of nucleotide 55 of
        complementary strand"
<220> FEATURE:
<221> NAME/KEY: misc_feature
<222> LOCATION: complement(95)
<223> OTHER INFORMATION: /note="A phosphate group is attached to the 5'
        carbon in the sugar-ring of the deoxyribose of nucleotide 95 of
        complementary strand"
<220> FEATURE:
<221> NAME/KEY: misc_feature
<222> LOCATION: 40^41
<223> OTHER INFORMATION: /note="Presence of a nick (no phosphodiester
        bond) between adjacent nucleotides 40 and 41"
<220> FEATURE:
<221> NAME/KEY: misc_feature
```

<222> LOCATION: complement(55^56)
<223> OTHER INFORMATION: /note="Presence of a nick (no phosphodiester
    bond) between adjacent nucleotides 55 and 56 of complementary
    strand"
<220> FEATURE:
<221> NAME/KEY: misc_feature
<222> LOCATION: 19..28
<223> OTHER INFORMATION: /note="Consensus sequence for NF kappa B
    transcription factor from nucleotide 19 to nucleotide 28"
<220> FEATURE:
<221> NAME/KEY: misc_feature
<222> LOCATION: 49..57
<223> OTHER INFORMATION: /note="Consensus sequence for STAT3
    transcription factor from nucleotide 49 to nucleotide 57"
<220> FEATURE:
<221> NAME/KEY: misc_feature
<222> LOCATION: 73..84
<223> OTHER INFORMATION: /note="Consensus sequence for ETS1
    transcription factor from nucleotide 73 to nucleotide 84"

<400> SEQUENCE: 11
ccttcggatt atcggacggg gactttccgt actcgttgct acgtgcattt cccgtaaatc    60
tccatggatc caggaagcac ttcctggtga cttgg                              95

<210> SEQ ID NO 12
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
    /note="Linear nicked blunt-ended duplec"
    /organism="Artificial Sequence"
<220> FEATURE:
<221> NAME/KEY: misc_feature
<222> LOCATION: 1
<223> OTHER INFORMATION: /note="A phosphate group is attached to the 5'
    carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
    carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
    carbon in the sugar-ring of the deoxyribose of nucleotide 55 of
    complementary strand"
<220> FEATURE:
<221> NAME/KEY: misc_feature
<222> LOCATION: complement(95)
<223> OTHER INFORMATION: /note="A phosphate group is attached to the 5'
    carbon in the sugar-ring of the deoxyribose of nucleotide 95 of
    complementary strand"
<220> FEATURE:
<221> NAME/KEY: misc_feature
<222> LOCATION: 40^41
<223> OTHER INFORMATION: /note="Presence of a nick (no phosphodiester
    bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
    bond) between adjacent nucleotides55 and 56 of complementary
    strand"
<220> FEATURE:
<221> NAME/KEY: misc_feature
<222> LOCATION: 7..90
<223> OTHER INFORMATION: /note="human telomeric sequence from nucleotide
    7 to nucleotide 90"

<400> SEQUENCE: 12
ccttggttag ggttagggtt agggttaggg ttagggttag ggttagggtt agggttaggg    60
ttagggttag ggttagggtt agggttaggg tttgg                                    95

<210> SEQ ID NO 13
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="Linear nicked blunt-ended duplex"
      /organism="Artificial Sequence"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: 55^56
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: complement(7)
<223> OTHER INFORMATION: /note="mismatch, nucleotide 7 of complementary
      strand is g"
<220> FEATURE:
<221> NAME/KEY: misc_feature
<222> LOCATION: complement(23)
<223> OTHER INFORMATION: /note="mismatch, nucleotide 23 of complementary
      strand is g"
<220> FEATURE:
<221> NAME/KEY: misc_feature
<222> LOCATION: complement(71)
<223> OTHER INFORMATION: /note="mismatch, nucleotide 71 of complementary
      strand is g"

<400> SEQUENCE: 13
ccaaggtctc aagactgatc tatagatcaa ctccttgcca ttgccgtacg agatctagcc    60
tctagctagt tgtgctgatc atactacgag catgg                               95

<210> SEQ ID NO 14
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="Linear nicked blunt-ended duplex"
      /organism="Artificial Sequence"
<220> FEATURE:
<221> NAME/KEY: misc_feature
<222> LOCATION: 1
<223> OTHER INFORMATION: /note="A phosphate group is attached to the 5' carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
     carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
     carbon in the sugar-ring of the deoxyribose of nucleotide 55 of
     complementary strand"
<220> FEATURE:
<221> NAME/KEY: misc_feature
<222> LOCATION: complement(95)
<223> OTHER INFORMATION: /note="A phosphate group is attached to the 5'
     carbon in the sugar-ring of the deoxyribose of nucleotide 95 of
     complementary strand"
<220> FEATURE:
<221> NAME/KEY: misc_feature
<222> LOCATION: 40^41
<223> OTHER INFORMATION: /note="Presence of a nick (no phosphodiester
     bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
     bond) between adjacent nucleotides 55 and 56 of complementary
     strand"
<220> FEATURE:
<221> NAME/KEY: misc_feature
<222> LOCATION: complement(41)
<223> OTHER INFORMATION: /note="nucleotide 71 on complementary strand
     is cyanine 3 dt"
<220> FEATURE:
<221> NAME/KEY: misc_feature
<222> LOCATION: complement(71)
<223> OTHER INFORMATION: /note="nucleotide 71 on complementary strand
     is 8-oxoguanine"

<400> SEQUENCE: 14
ccaaggcctc aagactgatc tacagatcaa ctccttgcca ttgccgtacg agatctagcc    60
tctagctagt cgtgctgatc atactacgag catgg                              95

<210> SEQ ID NO 15
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
     /note="Linear nicked blunt-ended duplex"
     /organism="Artificial Sequence"
<220> FEATURE:
<221> NAME/KEY: misc_feature
<222> LOCATION: 1
<223> OTHER INFORMATION: /note="A phosphate group is attached to the 5'
     carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
     carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
     carbon in the sugar-ring of the deoxyribose of nucleotide 55 of
     complementary strand"
<220> FEATURE:
<221> NAME/KEY: misc_feature
<222> LOCATION: complement(95)
<223> OTHER INFORMATION: /note="A phosphate group is attached to the 5'
     carbon in the sugar-ring of the deoxyribose of nucleotide 95 of
     complementary strand"

```
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: complement(20)
<223> OTHER INFORMATION: /note="nucleotide 20 on complementary strand
      is 8 oxoguanine"
<220> FEATURE:
<221> NAME/KEY: misc_feature
<222> LOCATION: complement(49)
<223> OTHER INFORMATION: /note="nucleotide 49 on complementary strand
      is 8 oxoguanine"

<400> SEQUENCE: 15
ccaaggcctc aagactgatc tacagatcaa ctccttgcca ttgccgtacg agatctagcc      60
tctagctagt cgtgctgatc atactacgag catgg                                95

<210> SEQ ID NO 16
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="Linear nicked blunt-ended duplex"
      /organism="Artificial Sequence"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: complement(85)
<223> OTHER INFORMATION: /note="nucleotide 85 on complementary strand is
      biotin dt"

<400> SEQUENCE: 16
```
ccttcggatt atcggacggc gctagcctgg ggactttcca gctggggact ttccagctgg    60
ggactttcca ggagattcag gatcaggtga cttgg                              95

<210> SEQ ID NO 17
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
     /note="Linear nicked blunt-ended duplex"
     /organism="Artificial Sequence"
<220> FEATURE:
<221> NAME/KEY: misc_feature
<222> LOCATION: 23
<223> OTHER INFORMATION: /note="nucleotide 23 is biotine dt"
<220> FEATURE:
<221> NAME/KEY: misc_feature
<222> LOCATION: 1
<223> OTHER INFORMATION: /note="A phosphate group is attached to the 5'
     carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
     carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
     carbon in the sugar-ring of the deoxyribose of nucleotide 55 of
     complementary strand"
<220> FEATURE:
<221> NAME/KEY: misc_feature
<222> LOCATION: complement(95)
<223> OTHER INFORMATION: /note="A phosphate group is attached to the 5'
     carbon in the sugar-ring of the deoxyribose of nucleotide 95 of
     complementary strand"
<220> FEATURE:
<221> NAME/KEY: misc_feature
<222> LOCATION: complement(85)
<223> OTHER INFORMATION: /note="nucleotide 85 on complementary strand
     is biotine dt"
<220> FEATURE:
<221> NAME/KEY: misc_feature
<222> LOCATION: 40^41
<223> OTHER INFORMATION: /note="Presence of a nick (no phosphodiester
     bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
     bond) between adjacent nucleotides 55 and 56 of complementary
     strand"

<400> SEQUENCE: 17
ccttcggatt atcggacggc gcnagcctgg ggactttcca gctggggact ttccagctgg    60
ggactttcca ggagattcag gatcaggtga cttgg                              95

<210> SEQ ID NO 18
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
     /note="Linear nicked blunt-ended duplex"
     /organism="Artificial Sequence"
<220> FEATURE:
<221> NAME/KEY: misc_feature
<222> LOCATION: 1

-continued

```
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: complement(85)
<223> OTHER INFORMATION: /note="nucleotide 85 on complementary strand
      is cyanin 3 dt"

<400> SEQUENCE: 18
ccttcggatt atcggacggc gctagcctgg ggactttcca gctggggact ttccagctgg    60
ggactttcca ggagattcag gatcaggtga cttgg                              95

<210> SEQ ID NO 19
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="Linear nickd blunt-ended duplex"
      /organism="Artificial Sequence"
<220> FEATURE:
<221> NAME/KEY: misc_feature
<222> LOCATION: 23
<223> OTHER INFORMATION: /note="nucleotide 23 is cyanine3 dt"
<220> FEATURE:
<221> NAME/KEY: misc_feature
<222> LOCATION: complement(85)
<223> OTHER INFORMATION: /note="nucleotide 85 on complementary strand
      is cyanine 3 dt"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
```

```
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"

<400> SEQUENCE: 19
ccttcggatt atcggacggc gcnagcctgg ggactttcca gctggggact ttccagctgg      60
ggactttcca ggagattcag gatcaggtga cttgg                                  95

<210> SEQ ID NO 20
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="Linear nicked blunt-ended duplex"
      /organism="Artificial Sequence"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 of complementary
      strand"
<220> FEATURE:
<221> NAME/KEY: misc_feature
<222> LOCATION: complement(85)
<223> OTHER INFORMATION: /note="nucleotide 85 on complementary strand is
      carboxyfluoroscein dt"

<400> SEQUENCE: 20
ccttcggatt atcggacggc gctagcctgg ggactttcca gctggggact ttccagctgg      60
ggactttcca ggagattcag gatcaggtga cttgg                                  95
```

```
<210> SEQ ID NO 21
<211> LENGTH: 95
<212> TYPE: DNA
<213> ORGANISM: Artificial Sequence
<220> FEATURE:
<221> NAME/KEY: source
<222> LOCATION: 1..95
<223> OTHER INFORMATION: /mol_type="unassigned DNA"
      /note="Linear nicked blunt-ended sequence"
      /organism="Artificial Sequence"
<220> FEATURE:
<221> NAME/KEY: misc_feature
<222> LOCATION: 23
<223> OTHER INFORMATION: /note="nucleotide 23 is carboxyfluoroscein dt"
<220> FEATURE:
<221> NAME/KEY: misc_feature
<222> LOCATION: complement(85)
<223> OTHER INFORMATION: /note="nucleotide 85 on complementary strand is
      carboxyfluoroscein dt"
<220> FEATURE:
<221> NAME/KEY: misc_feature
<222> LOCATION: 1
<223> OTHER INFORMATION: /note="A phosphate group is attached to the 5'
      carbon in the sugar-ring of the deoxyribose of nucleotide 1"
<220> FEATURE:
<221> NAME/KEY: misc_feature
<222> LOCATION: 41
<223> OTHER INFORMATION: /note="A phosphate group is attached to the 5'
      carbon in the sugar-ring of the deoxyribose of nucleotide 41"
<220> FEATURE:
<221> NAME/KEY: misc_feature
<222> LOCATION: complement(55)
<223> OTHER INFORMATION: /note="A phosphate group is attached to the 5'
      carbon in the sugar-ring of the deoxyribose of nucleotide 55 of
      complementary strand"
<220> FEATURE:
<221> NAME/KEY: misc_feature
<222> LOCATION: complement(95)
<223> OTHER INFORMATION: /note="A phosphate group is attached to the 5'
      carbon in the sugar-ring of the deoxyribose of nucleotide 95 of
      complementary strand"
<220> FEATURE:
<221> NAME/KEY: misc_feature
<222> LOCATION: 40^41
<223> OTHER INFORMATION: /note="Presence of a nick (no phosphodiester
      bond) between adjacent nucleotides 40 and 41"
<220> FEATURE:
<221> NAME/KEY: misc_feature
<222> LOCATION: complement(55^56)
<223> OTHER INFORMATION: /note="Presence of a nick (no phosphodiester
      bond) between adjacent nucleotides 55 and 56 on complementary
      strand"

<400> SEQUENCE: 21
ccttcggatt atcggacggc gcnagcctgg ggactttcca gctggggact ttccagctgg     60
ggactttcca ggagattcag gatcaggtga cttgg                                95
```

The invention claimed is:

1. A method for the in vitro production of DNA minicircles having between 80 base pairs and less than 250 base pairs, said method comprising steps of:
   a) providing nicked double-stranded oligodeoxynucleotides blunt-ended substrates having at least one phosphorylated 5' end, wherein the nicked double-stranded oligodeoxynucleotides substrates provided comprise between 80 base pairs and less than 250 base pairs;
   b) performing a ligase-mediated circularization on a reaction mixture comprising the said nicked double-stranded oligodeoxynucleotides substrates and a DNA bending protein, wherein said DNA bending protein is a non-sequence specific HMBG protein; and
   c) obtaining DNA minicircles having between 80 base pairs and less than 250 base pairs.

2. The method according to claim 1, wherein step c) comprises eliminating reaction contaminants.

3. The method according to claim 2, wherein step c) of eliminating reaction contaminants comprises the addition of at least one enzyme selected from the group consisting of the proteases and the exonucleases.

4. The method according to claim 1, wherein the DNA bending protein is an HMGB1 protein.

5. The method according to claim 1, wherein the nicked double-stranded oligodeoxynucleotides substrates provided at step a), exhibit an overlapping inter-nick region comprised between 10 and 20 base pairs.

6. The method according to claim 1, wherein the nicked double-stranded oligodeoxynucleotides substrates provided at step a) have two phosphorylated 5' ends and the DNA minicircles obtained at step c) are double-stranded closed relaxed DNA minicircles.

7. The method according to claim 2, wherein the nicked double-stranded oligodeoxynucleotides blunt-ended substrates provided at step a) have only one phosphorylated 5' end, and the DNA minicircles obtained at step c) are single-stranded DNA minicircles.

8. The method according to claim 7, further comprising steps of:
   d) adding a linear oligonucleotide complementary to the strand having an unphosphorylated 5' end of the nicked double-stranded oligodeoxynucleotides blunt-ended substrates strands of step a); and
   e) obtaining nicked double-stranded DNA minicircles.

9. The method according to claim 1 comprising steps of:
   a) providing nicked double-stranded oligodeoxynucleotides blunt-ended substrates having only one phosphorylated 5' end, wherein the nicked double-stranded oligodeoxynucleotides substrates provided comprise between 80 base pairs and less than 250 base pairs,
   b) performing a ligase-mediated circularization on a reaction mixture comprising the said nicked double-stranded oligodeoxynucleotides substrates and a DNA bending protein, wherein said DNA bending protein is a non-sequence specific HMBG protein
   c) obtaining nicked double-stranded DNA minicircles having between 80 base pairs and less than 250 base pairs,
   d) adding a kinase to the nicked double-stranded DNA minicircles obtained at step c),
   e) ligating the said nicked double-stranded DNA minicircles in the presence of a DNA intercalator,
   f) obtaining supercoiled DNA minicircles having between 80 base pairs and less than 250 base pairs.

10. The method according to claim 1, wherein the nicked double-stranded oligodeoxynucleotides blunt-ended substrates having at least one phosphorylated 5' end further comprise at least one sequence functionalization selected from the group consisting of protein putative binding sites, DNA binding sites, chemical functionalities, DNA base mismatches.

11. The method according to claim 10, wherein putative protein binding sites include binding sites for proteins selected from the group consisting of transcription factors, DNA repair proteins, telomeric protein, remodelling factors, helicases, polymerases, architectural proteins, topoisomerases and restriction endonucleases.

12. The method according to claim 10, wherein the chemical functionalities include site-specifically placed base modifications and site-specifically placed labels.

* * * * *